United States Patent
Esvelt et al.

(10) Patent No.: US 10,752,906 B2
(45) Date of Patent: Aug. 25, 2020

(54) PRECISE MICROBIOTA ENGINEERING AT THE CELLULAR LEVEL

(71) Applicant: President and Fellows of Harvard College, Cambridge, MA (US)

(72) Inventors: Kevin M. Esvelt, Auburndale, MA (US); Stephanie Yaung, San Jose, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 108 days.

(21) Appl. No.: 15/034,682

(22) PCT Filed: Nov. 5, 2014

(86) PCT No.: PCT/US2014/063994
§ 371 (c)(1),
(2) Date: May 5, 2016

(87) PCT Pub. No.: WO2015/069682
PCT Pub. Date: May 14, 2015

(65) Prior Publication Data
US 2016/0348120 A1    Dec. 1, 2016

Related U.S. Application Data

(60) Provisional application No. 61/900,002, filed on Nov. 5, 2013.

(51) Int. Cl.
| | |
|---|---|
| C12N 15/70 | (2006.01) |
| C12N 1/20 | (2006.01) |
| C12N 15/113 | (2010.01) |
| C12N 1/38 | (2006.01) |
| A61K 35/74 | (2015.01) |
| C12N 15/90 | (2006.01) |

(52) U.S. Cl.
CPC .............. *C12N 15/70* (2013.01); *A61K 35/74* (2013.01); *C12N 1/20* (2013.01); *C12N 1/38* (2013.01); *C12N 15/1131* (2013.01); *C12N 15/902* (2013.01); *C12N 2310/10* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 2013/0288251 A1 | 10/2013 | Horvath et al. | |
| 2014/0068797 A1* | 3/2014 | Doudna | C12N 15/102 800/18 |

OTHER PUBLICATIONS

Stern et al. Genome Research, 22:1985-1994 (Year: 2012).*
Esvelt 2014 (Concerning RNA-guided gene drives for the alteration of wild populations; eLife 2014; 3:e03401. DOI: 10.7554/eLIfe.03401) (Year: 2014).*
Jinek et al. 2012 (A programmable dual RNA-guided DNA endonuclease in adaptive bacterial immunity; Science 337(6096): 816-821) (Year: 2012).*
Esvelt et al. 2013 (Genome-scale engineering for systems and synthetic biology; Molecular Systems Biology 9:641: 1-17) (Year: 2013).*
International Search Report issued in corresponding International Application No. PCT/US 14/63994, dated Apr. 23, 2015.
Charpentier et al., Biotechnology: Rewriting a Genome, Nature 495, pp. 50-52, Abstract, Figure 1, Mar. 2013.
Esvelt et al., Orthogonal Cas9 Proteins for RNA-Guided Gene Regulation and Editing, Nat Methods, 10(11), pp. 1-18, Sep. 2013.
Jinek et al., A Programmable Dual-RNA-Guided DNA Endonuclease in Adaptive Bacterial Immunity, Science, vol. 337, No. 6096, pp. 816-821, Aug. 17, 2012.

* cited by examiner

*Primary Examiner* — Mary Maille Lyons
(74) *Attorney, Agent, or Firm* — Banner & Witcoff, Ltd.

(57) ABSTRACT

Stably immunized cells and methods of making stably immunized cells are provided. Methods of altering the microbiota of an ecological environment are provided. Methods of modifying target chromosomes are provided. Methods of delivering genetic material to target cells are provided.

15 Claims, 8 Drawing Sheets

Specification includes a Sequence Listing.

SEQUENCE LISTING

<160> NUMBER OF SEQ ID NOS: 1

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300
```

```
Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720
```

-continued

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val

-continued

|  |  |  |  | 1130 |  |  |  | 1135 |  |  |  | 1140 |  |  |
|---|---|---|---|---|---|---|---|---|---|---|---|---|---|---|
| Leu | Val 1145 | Val | Ala | Lys | Val | Glu 1150 | Lys | Gly | Lys | Ser | Lys 1155 | Lys | Leu | Lys |
| Ser | Val 1160 | Lys | Glu | Leu | Leu | Gly 1165 | Ile | Thr | Ile | Met | Glu 1170 | Arg | Ser | Ser |
| Phe | Glu 1175 | Lys | Asn | Pro | Ile | Asp 1180 | Phe | Leu | Glu | Ala | Lys 1185 | Gly | Tyr | Lys |
| Glu | Val 1190 | Lys | Lys | Asp | Leu | Ile 1195 | Ile | Lys | Leu | Pro | Lys 1200 | Tyr | Ser | Leu |
| Phe | Glu 1205 | Leu | Glu | Asn | Gly | Arg 1210 | Lys | Arg | Met | Leu | Ala 1215 | Ser | Ala | Gly |
| Glu | Leu 1220 | Gln | Lys | Gly | Asn | Glu 1225 | Leu | Ala | Leu | Pro | Ser 1230 | Lys | Tyr | Val |
| Asn | Phe 1235 | Leu | Tyr | Leu | Ala | Ser 1240 | His | Tyr | Glu | Lys | Leu 1245 | Lys | Gly | Ser |
| Pro | Glu 1250 | Asp | Asn | Glu | Gln | Lys 1255 | Gln | Leu | Phe | Val | Glu 1260 | Gln | His | Lys |
| His | Tyr 1265 | Leu | Asp | Glu | Ile | Ile 1270 | Glu | Gln | Ile | Ser | Glu 1275 | Phe | Ser | Lys |
| Arg | Val 1280 | Ile | Leu | Ala | Asp | Ala 1285 | Asn | Leu | Asp | Lys | Val 1290 | Leu | Ser | Ala |
| Tyr | Asn 1295 | Lys | His | Arg | Asp | Lys 1300 | Pro | Ile | Arg | Glu | Gln 1305 | Ala | Glu | Asn |
| Ile | Ile 1310 | His | Leu | Phe | Thr | Leu 1315 | Thr | Asn | Leu | Gly | Ala 1320 | Pro | Ala | Ala |
| Phe | Lys 1325 | Tyr | Phe | Asp | Thr | Thr 1330 | Ile | Asp | Arg | Lys | Arg 1335 | Tyr | Thr | Ser |
| Thr | Lys 1340 | Glu | Val | Leu | Asp | Ala 1345 | Thr | Leu | Ile | His | Gln 1350 | Ser | Ile | Thr |
| Gly | Leu 1355 | Tyr | Glu | Thr | Arg | Ile 1360 | Asp | Leu | Ser | Gln | Leu 1365 | Gly | Gly | Asp |

PRECISE MICROBIOTA ENGINEERING AT THE CELLULAR LEVEL

RELATED APPLICATION DATA

This application is a National Stage Application under 35 U.S.C. 371 of co-pending PCT application number PCT/US14/63994 designating the United States and filed Nov. 5, 2014; which claims the benefit of U.S. provisional application No. 61/900,002 and filed Nov. 5, 2013 each of which are hereby incorporated by reference in their entireties.

STATEMENT OF GOVERNMENT INTERESTS

This invention was made with government support under DE-FG02-02ER63445 awarded by Department of Energy and under N66001-12-C-4040 awarded by Defense Advanced Research Projects Agency. The government has certain rights in the invention.

BACKGROUND

The microbial communities living within our bodies help us resist acute infection, regulate our immune responses, and play important roles in our nutrition and metabolism. Unlike our own cells, our microbial passengers can be genetically modified or replaced without risking cancer or immune rejection. Despite these advantages, very few tools capable of making precise or lasting changes to our internal ecosystems are available. Reliable methods of controlling the composition of these communities could open the door to a new medicinal paradigm focused on immunizing microbes against pathogenesis and harnessing them as living therapeutics.

Numerically, humankind is more microbial than human. Our bodies are comprised of $\sim 10^{13}$ human cells and $\sim 10^{14}$ microbes (Ley et al. Cell 2006 February; 124(4):837-848; Qin et al. Nature 2010 March; 464(7285):59-65). The composition of these microbial communities, collectively termed the microbiota, has a commensurately dramatic impact on human health and disease (Lawley et al. Immunology 2013 January; 138(1):1-11; Lozupone et al. Nature 2012 September; 489(7415):220-230. Healthy and diverse microbial communities prevent pathogens from invading our bodies by competing for space and nutrients (Leatham et al. Infect. Immun. 2009 July; 77(7):2876-2886; Kamada et al. Nat. Immunol. 2013 July; 14(7):685-690) and clearing existing infections (Barman et al. Infect. Immun. 2008 March; 76(3): 907-915; Endt et al. PLoS Pathog. 2010; 6(9):e1001097). The composition of the microbiota is an equally strong determinant of chronic disorders, from *H. pylori*-induced gastric disease (Marshall et al. Lancet 1984 June; 1(8390): 1311-1315; Salama et al. Nat. Rev. Microbiol. 2013 June; 11(6):385-399) to obesity (Turnbaugh et al. Nature 2006 December; 444(7122):1027-1031; Ridaura et al. Science 2013 September; 341(6150):1241214) metabolic syndrome (Vrieze et al. Gastroenterology 2012 October; 143(4):913-916.e7), and the complexities of inflammatory bowel disease (Kamada, Supra; Abraham et al. Gastroenterology 2011 May; 140(6):1729-1737; Horwitz et al. Inflamm. Bowel Dis. 2007 April; 13(4):490-500). Even the dramatic metabolic benefits conferred by gastric bypass surgery may be largely due to changes in the microbiota (Liou et al. Sci Transl Med 2013 March; 5(178):178ra41).

Much of our newfound knowledge stems from the herculean efforts of researchers involved in the Human Microbiome Project and MetaHIT. These major initiatives and related studies employing metagenomic sequencing to paint comprehensive portraits of the genes and species involved in health and disease (Human Microbiome Project Consortium. A framework for human microbiome research. Nature 2012 June; 486(7402):215-221; Human Microbiome Project Consortium. Structure, function and diversity of the healthy human microbiome. Nature 2012 June; 486(7402):207-214; Turnbaugh et al. Sci Transl Med 2009 November; 1(6): 6ra14; Le Chatelier et al. Nature 2013 August; 500(7464): 541-546; Cotillard et al. Nature 2013 August; 500(7464): 585-588).

Unfortunately, there has been no comparable effort to develop interventions capable of altering pictures of disease to ones of health. Antibiotics, fecal transplantation, and dietary changes are all highly effective treatments for various gastric conditions (Vrieze, Supra; Estruch et al. N. Engl. J. Med. 2013 April; 368(14):1279-1290; Smoot et al. Am. J. Gastroenterol. 1999 April; 94(4):955-958; Pimentel et al. Am. J. Gastroenterol. 2000 December; 95(12):3503-3506; Van Nood et al. N. Engl. J. Med. 2013 January; 368(5):407-415), but using them to make precise changes to the microbiota is tantamount to sculpting a forest with fire (Lozupone, Supra). Antibiotics typically result in losses of community diversity and stability that may cause disease (Larson et al. Lancet 1978 May; 1(8073):1063-1066; Cho et al. Nature 2012 August; 488(7413):621-626) and can be permanent (Dethlefsen et al. PLoS Biol. 2008 November; 6(11):e280; Antonopoulos et al. Infect. Immun. 2009 June; 77(6):2367-2375); in these cases, transplanting the microbiota of a healthy donor cannot restore these losses (Manichanh et al. Genome Res. 2010 October; 20(10):1411-1419) as transplanted communities typically revert to that of the recipient (McNulty et al. Sci Transl Med 2011 October; 3(106): 106ra106; Nieuwdorp Gastroenterology 2013 April; 144(4): e20-21) except when the latter is effectively eliminated (Van Nood, Supra). Similarly, ingesting beneficial probiotic species is analogous to scattering apple seeds in the woods, as introduced species are normally eliminated from the gut due to colonization resistance by existing species that already occupy all available ecological niches (McNulty, Supra; Lee et al. Nature 2013 September; 501(7467):426-429; Maltby et al. PLoS ONE 2013; 8(1):e53957).

The absence of methods allowing the cellular and genetic composition of the microbiota to be stably altered has severely impaired mankind's scientific understanding. Even as the ability to knock out and overexpress individual genes has transformed knowledge of cellular complexity and function, developing equivalent capabilities for manipulating the genes and species of the microbiota will be essential to unraveling the still greater complexity of our internal ecosystems.

To sculpt the microbiota, the evolutionary fitness of individual genes and species must be controlled. Phages and mobile genetic parasites might be similarly harnessed to engineer populations of bacteria. Phage predation is both highly specific to individual species and of great ecological importance (Abedon, ST. Bacteriophage ecology: population growth, evolution, and impact of bacterial viruses. Cambridge: Cambridge University Press; 2008), with a long history of therapeutic use against pathogenic bacteria in Eastern Europe (Abedon Bacteriophage 2011; 1(2):66-85) and a low bar for FDA approval (Brussow Virology 2012 December; 434(2):138-142). Similarly, mobile genetic elements are known to readily spread through the microbiota (Stecher et al. Proc. Natl. Acad. Sci. U.S.A. 2012 January; 109(4):1269-1274) and have been proposed as vehicles to deliver lethal genes (Filutowicz et al. Plasmid 2008 July; 60(1):38-44; Fairhead Drug News Perspect. 2009 May; 22(4):197-203).

Editing the genomes of native species or replacing them with protective strains could immunize microbial ecosystems against dysbiosis, antibiotic resistance, and pathogenicity. Stable populations of engineered cells could secrete consistent levels of therapeutic and regulatory molecules for the in situ treatment of disease.

SUMMARY

The need remains to target or exempt particular strains of bacteria or, still more difficult, genes, and maintain such changes in the face of natural selection. RNA-guided Cas9 nuclease can be used to fulfill these needs.

Bacterial and archaeal CRISPR-Cas systems rely on short guide RNAs in complex with Cas proteins to direct degradation of complementary sequences present within invading foreign nucleic acid. See Deltcheva, E. et al. Nature 471: 602-607 (2011); Gasiunas et al. *Proceedings of the National Academy of Sciences of the United States of America* 109: E2579-2586 (2012); Jinek et al. Science 337:816-821 (2012); Sapranauskas, R. et al. Nucleic acids research 39:9275-9282 (2011); and Bhaya et al. Annual review of genetics 45:273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al. Journal of Bacteriology 190:1390 (February, 2008).

The effector component of type II CRISPR systems provide bacteria with acquired immunity in nature (Deltcheva et al. Nature 2011 March; 471(7340):602-607). Cas9 has been developed into a revolutionary tool to engineer (Mali et al. Science 2013 February; 339(6121):823-826; Cong et al. Science 2013 February; 339(6121):819-823. Jinek et al. Science 2012 August; 337(6096):816-821) and regulate (Mali et al. Nat. Biotechnol. 2013 September; 31(9):833-838; Gilbert et al. Cell 2013 July; 154(2):442-451; Esvelt et al. Nat. Methods 2013 September) the genomes of numerous organisms (Mali et al. Nat. Methods 2013 September; 10(10):957-963). Because Cas9 can be readily targeted to cleave almost any given DNA sequence by expressing a homologous "spacer" within a CRISPR locus, aspects of this invention are directed to its use to immunize cells against both phages and pathogenic genes. (See FIG. 1.).

In certain exemplary embodiments, a method of producing a stably immunized cell (e.g., a microbial cell, e.g., a bacterial cell) is provided. The method comprises the steps of introducing into the bacterial cell a foreign nucleic acid sequence encoding a plurality of ribonucleic acid sequences, wherein one or more of the plurality of ribonucleic acid sequences is complementary to an exogenous phage nucleic acid sequence, and one or more of the plurality of ribonucleic acid sequences is complementary to an exogenous virulence nucleic acid sequence, wherein the bacterial cell expresses the foreign nucleic acid sequence encoding a plurality of ribonucleic acid sequences, and wherein at least one of the plurality of ribonucleic acid sequences binds to a complementary exogenous phage nucleic acid sequence or an exogenous virulence nucleic acid sequence, and an RNA guided enzyme interacts with one or more of the plurality of ribonucleic acid sequences and cleaves the exogenous phage nucleic acid sequence or the exogenous virulence nucleic acid sequence in a site specific manner. In certain exemplary embodiments, a method of producing a stably immunized cell (e.g., a microbial cell, e.g., a bacterial cell) is provided. The method comprises the steps of introducing into the bacterial cell a foreign nucleic acid sequence encoding a plurality of ribonucleic acid sequences, wherein one or more of the plurality of ribonucleic acid sequences is complementary to an exogenous phage nucleic acid sequence, or one or more of the plurality of ribonucleic acid sequences is complementary to an exogenous virulence nucleic acid sequence, wherein the bacterial cell expresses the foreign nucleic acid sequence encoding a plurality of ribonucleic acid sequences, and wherein at least one of the plurality of ribonucleic acid sequences binds to a complementary exogenous phage nucleic acid sequence or an exogenous virulence nucleic acid sequence, and an RNA guided enzyme interacts with one or more of the plurality of ribonucleic acid sequences and cleaves the exogenous phage nucleic acid sequence or the exogenous virulence nucleic acid sequence in a site specific manner. In certain aspects, the method includes the step of introducing into the bacterial cell a second foreign nucleic acid encoding an RNA guided enzyme that interacts with one or more of the plurality of ribonucleic acid sequences and cleaves exogenous nucleic acid sequences in a site specific manner.

In certain aspects, the RNA guided enzyme is exogenous or orthogonal Cas9. In certain aspects, at least five of the plurality of ribonucleic acid sequences bind to complementary exogenous phage nucleic acid sequences (e.g., conserved sequences) and/or at least five of the plurality of ribonucleic acid sequences bind to complementary exogenous virulence nucleic acid sequences. In certain aspects, one or more of the plurality of ribonucleic acid sequences is complementary to an exogenous nucleic acid sequence encoding a product that is toxic to the bacterial cell or to a host of the bacterial cell. In other aspects, the foreign nucleic acid sequence is provided as a mobile genetic element. In still other aspects, the foreign nucleic acid sequence introduced into the bacterial cell by a method selected from the group consisting of bacterial conjugation, infection, transfection and transformation. In still other aspects, the bacterial cell is non-pathogenic to a host. In other aspects one, two or a plurality of foreign nucleic acid sequences are integrated into the genome of the bacterial cell using homologous recombination. In certain aspects, the plurality of ribonucleic acid sequences is selected from the group consisting of pre-crRNA, crRNA, tracrRNA, guide RNA, and any combinations thereof.

In certain exemplary embodiments, a stably immunized cell (e.g., a microbial (e.g., bacterial) cell) is provided. The cell includes a foreign nucleic acid sequence encoding a plurality of ribonucleic acid sequences, wherein one or more of the plurality of ribonucleic acid sequences is complementary to an exogenous phage nucleic acid sequence and one or more of the plurality of ribonucleic acid sequences is complementary to an exogenous virulence nucleic acid sequence, and an RNA guided enzyme that interacts with one or more of the plurality of ribonucleic acid sequences to cleave the exogenous phage nucleic acid sequence or the exogenous virulence nucleic acid sequence in a site specific manner. In certain exemplary embodiments, a stably immunized cell (e.g., a microbial (e.g., bacterial) cell) is provided. The cell includes a foreign nucleic acid sequence encoding a plurality of ribonucleic acid sequences, wherein one or more of the plurality of ribonucleic acid sequences is complementary to an exogenous phage nucleic acid sequence or one or more of the plurality of ribonucleic acid sequences is complementary to an exogenous virulence nucleic acid sequence, and an RNA guided enzyme that interacts with one or more of the plurality of ribonucleic acid sequences to cleave the exogenous phage nucleic acid sequence or the exogenous virulence nucleic acid sequence in a site specific manner. In certain aspects, wherein the RNA guided enzyme is endogenous Cas9 or orthogonal Cas9. In certain aspects at least ten of the plurality of ribonucleic acid sequences bind to complementary exogenous phage nucleic acid sequences (e.g., conserved sequences) and/or at least ten of the plurality of ribonucleic acid sequences bind to complementary exogenous virulence nucleic acid sequences. In other aspects, the bacterial cell is non-pathogenic to a host. In other aspects one, two or a plurality of foreign nucleic acid sequences are integrated into the genome of the bacterial cell using homologous recombination. In certain aspects, the plurality of ribonucleic acid sequences is selected from the group consisting of pre-crRNA, crRNA, tracrRNA, guide RNA, and any combinations thereof.

In certain exemplary embodiments, a method of altering a microbe population in an ecological environment is provided. The method includes the steps of depleting one or more target microbe species from the ecological environment using a pathogen, contacting the ecological environment with at least one immune microbe engineered to have immunity against the pathogen, and allowing the at least one immune microbe to colonize the ecological environment in place of the depleted target microbe species. In certain aspects, the ecological environment is an individual and/or a gut. In certain aspects, the pathogen is a bacteriophage. In other aspects, the immune microbe has Cas9-mediated immunity.

In certain exemplary embodiments, a method of genetically modifying a bacterial chromosome is provided. The method includes the steps of providing a recipient bacterium expressing crRNA sequences or gRNA sequences at a genomic site for insertion, wherein the genomic site for insertion is flanked by a recombination site on either side, providing a donor bacterium (plasmid) expressing a nucleic acid sequence encoding Cas9, a nucleic acid sequence having homology to the genomic site for insertion, and a foreign nucleic acid sequence, conjugating the plasmid into the recipient bacterium, allowing Cas9 to cleave the recipient cell chromosome at the genomic site for insertion, and allowing the cell to use homologous repair with the plasmid as a template to modify the target chromosome to include the foreign nucleic acid sequence. In certain aspects, the recombination site is a chi site.

In certain exemplary embodiments, a method of delivering a mobile genetic element to a population of recipient microbes is provided. The method includes the steps of providing a large population of donor microbes comprising mobile genetic elements encoding Cas9, contacting a population of recipient microbes with the population of donor microbes so as to mimic "bloom" conditions (Stecher et al. Proc. Natl. Acad. Sci. U.S.A. 2012 January; 109(4):1269-1274) in which most recipient microbes will contact at least one donor microbe, and conjugating the mobile genetic elements into the population of recipient microbes. In certain aspects, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of the recipient microbes receive at least one mobile genetic element.

DETAILED DESCRIPTION

Figure 1:
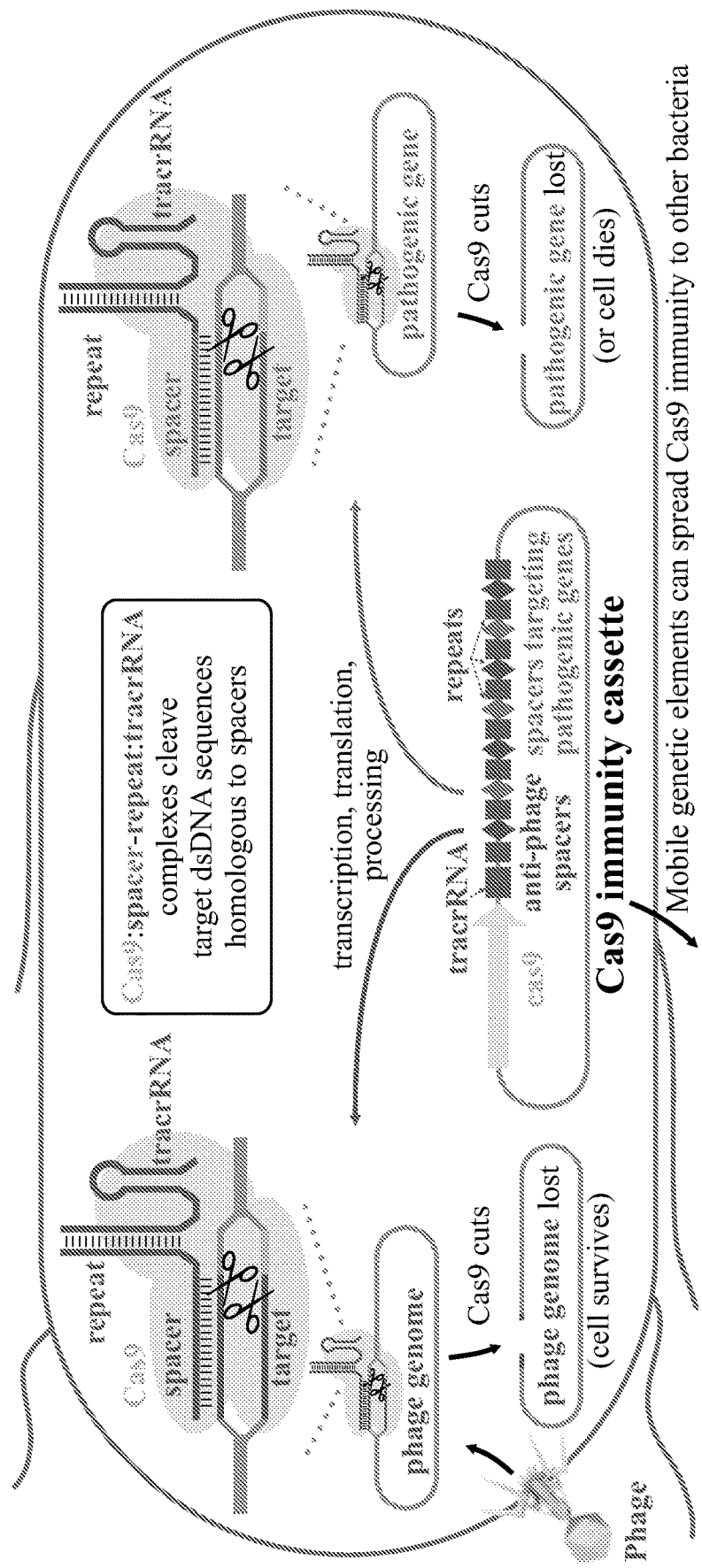
FIG. 1 schematically depicts cassettes providing bacterial cells with Cas9 immunity against phages and pathogenic genes.

Supporting references listed herein may be referred to by square brackets. It is to be understood that the superscript refers to the reference as if fully set forth to support a particular statement.

The subject disclosure provides precise methods of altering the cellular and genetic composition of the microbiota of an ecological environment, e.g., in an individual. Such methods are useful, e.g., for the treatment of enteric disease.

Accordingly, embodiments of the present disclosure are directed to methods of precisely replacing targeted bacterial strains with a related strain. In certain aspects, a mixture of phages can be used to deplete target species within a complex ecological environment. The replacement strain can be engineered using the RNA-guided Cas9 nuclease to be immune to one or more or all the phages specific for that strain. The engineered strain is then released into the ecological environment, where it will colonize the vacant ecological niche.

Other embodiments of the present disclosure are directed to methods of immunizing existing microbes against target genes within a complex ecology. In certain aspects, genetic elements carrying the RNA-guided Cas9 nuclease are delivered to target cells in such a way that they are copied into the genome. Cells with the targeted genes will either die or lose the genes. This novel method provides the stable modification of non-pathogenic organisms to prevent them from becoming pathogenic.

Yet other embodiments of the present disclosure are directed to methods of copying arbitrary-length DNA cassettes to and from chromosomes using Cas9. In certain aspects, a conjugative plasmid with a selectable marker, Cas9, and the following insert: (Homology to insertion location in target recipient cell genome)(homology flanking target DNA cassette)(recombinogenic chi site or equivalent for cell encoding target DNA cassette)(target sequence for Cas9 cutting)(selectable or screenable marker)(target sequence for Cas9 cutting)(recombinogenic chi site or equivalent for cell encoding target DNA cassette)(homology flanking target DNA cassette)(homology to insertion location in target recipient cell genome). Cells are engineered with target DNA cassette to express crRNA/sgRNA targeting the Cas9 target sequence. The plasmid is conjugated into a cell bearing a target DNA cassette. The Cas9 cuts plasmid at target sequences. The cell uses homology-directed repair with the chromosomal homology to fix double-strand break, thereby copying the target DNA cassette into the plasmid. Recipient cells are engineered to express crRNA/sgRNA the genomic site for insertion (in certain aspects, this site is flanked by recombinogenic chi sites if a bacterium). The plasmid is conjugated into a recipient cell. Cas9 cuts recipient cell chromosome at site for insertion. The cell uses homology-directed repair to fix double-strand break using the homology on the plasmid as a template, thereby copying the target DNA cassette into the chromosome.

An identical procedure can be used to copy a cassette from the chromosome into a mobile element. This allows a conjugative plasmid delivered into a host cell to be cut and repaired using the cassette from the host cell as a template, thereby acquiring a copy of the cassette, then conjugated into a recipient cell. Optionally, the cassette may be copied into the genome of the recipient cell using the above method.

Embodiments of the present disclosure are based on the use of DNA binding proteins to cleave nucleic acid sequences (e.g., exogenous DNA, endogenous DNA (e.g., genomic DNA) and the like) in an RNA-dependent manner. Such DNA binding proteins are readily known to those of skill in the art to bind to DNA for various purposes. Such DNA binding proteins may be naturally occurring. DNA binding proteins included within the scope of the present disclosure include those which may be guided by RNA, referred to herein as guide RNA. According to this aspect, the guide RNA and the RNA guided DNA binding protein form a co-localization complex at the DNA. Such DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al. Microbiology 2011 June; 9:467-477 including all supplementary information hereby incorporated by reference in its entirety.

Embodiments of the present disclosure are based on the use of foreign DNA, nuclease enzymes such as DNA binding proteins and guide RNAs to co-localize to DNA and digest or cut the DNA with insertion of the foreign DNA, such as by homologous recombination. Such DNA binding proteins are readily known to those of skill in the art to bind to DNA for various purposes. Such DNA binding proteins may be naturally occurring. DNA binding proteins included within the scope of the present disclosure include those which may be guided by RNA, referred to herein as guide RNA. According to this aspect, the guide RNA and the RNA guided DNA binding protein form a co-localization complex at the DNA. Such DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al. Microbiology 2011 June; 9:467-477 including all supplementary information hereby incorporated by reference in its entirety.

Exemplary DNA binding proteins having nuclease activity function to nick or cut double stranded DNA. Such nuclease activity may result from the DNA binding protein having one or more polypeptide sequences exhibiting nuclease activity. Such exemplary DNA binding proteins may have two separate nuclease domains with each domain responsible for cutting or nicking a particular strand of the double stranded DNA. Exemplary polypeptide sequences having nuclease activity known to those of skill in the art include the McrA-HNH nuclease related domain and the RuvC-like nuclease domain. Accordingly, exemplary DNA binding proteins are those that in nature contain one or more of the McrA-HNH nuclease related domain and the RuvC-like nuclease domain.

An exemplary DNA binding protein is an RNA guided DNA binding protein of a Type II CRISPR System. An exemplary DNA binding protein is a Cas9 protein.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinke et al. Science 337:816-821 (2012) hereby incorporated by reference in its entirety. Cas9 proteins are known to exist in many Type II CRISPR systems including the following as identified in the supplementary information to Makarova et al. Microbiology 2011 June; 9:467-477; *Methanococcus maripaludis* C7; *Corynebacterium diphtheriae*; *Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua*; *Lactobacillus casei*; *Lactobacillus rhamnosus* GG; *Lactobacillus salivarius* UCC118; *Streptococcus agalactiae* A909; *Streptococcus agalactiae*

NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans*; *Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum; Mycoplasma* mobile 163K; *Mycoplasma penetrans; Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni doylei* 269 97; *Campylobacter jejuni* 81116; *Campylobacter jejuni; Campylobacter lari* RM2100; *Helicobacter hepaticus; Wolinella succinogenes; Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida; Francisella tularensis novicida* U112; *Francisella tularensis* holarctica; *Francisella tularensis* FSC 198; *Francisella tularensis tularensis; Francisella tularensis* WY96-3418; and *Treponema denticola* ATCC 35405. Accordingly, aspects of the present disclosure are directed to a Cas9 protein present in a Type II CRISPR system, which has been rendered nuclease null or which has been rendered a nickase as described herein.

The Cas9 protein may be referred by one of skill in the art in the literature as Csn1. The *S. pyogenes* Cas9 protein sequence that is the subject of experiments described herein is shown below. See Deltcheva et al. Nature 471:602-607 (2011) hereby incorporated by reference in its entirety.

```
                                     (SEQ ID NO: 1)
MDKKYSIGLDIGTNSVGWAVITDEYKVPSKKFKVLGNTDRHSIKKNLIG

ALLFDSGETAEATRLKRTARRRYTRRKNRICYLQEIFSNEMAKVDDSFF

HRLEESFLVEEDKKHERHPIFGNIVDEVAYHEKYPTIYHLRKKLVDSTD

KADLRLIYLALAHMIKFRGHFLIEGDLNPDNSDVDKLFIQLVQTYNQLF

EENPINASGVDAKAILSARLSKSRRLENLIAQLPGEKKNGLFGNLIALS

LGLTPNFKSNFDLAEDAKLQLSKDTYDDDLDNLLAQIGDQYADLFLAAK

NLSDAILLSDILRVNTEITKAPLSASMIKRYDEHHQDLTLLKALVRQQL

PEKYKEIFFDQSKNGYAGYIDGGASQEEFYKFIKPILEKMDGTEELLVK
```

-continued

```
LNREDLLRKQRTFDNGSIPHQIHLGELHAILRRQEDFYPFLKDNREKIE

KILTFRIPYYVGPLARGNSRFAWMTRKSEETITPWNFEEVVDKGASAQS

FIERMTNFDKNLPNEKVLPKHSLLYEYFTVYNELTKVKYVTEGMRKPAF

LSGEQKKAIVDLLFKTNRKVTVKQLKEDYFKKIECFDSVEISGVEDRFN

ASLGTYHDLLKIIKDKDFLDNEENEDILEDIVLTLTLFEDREMIEERLK

TYAHLFDDKVMKQLKRRRYTGWGRLSRKLINGIRDKQSGKTILDFLKSD

GFANRNFMQLIHDDSLTFKEDIQKAQVSGQGDSLHEHIANLAGSPAIKK

GILQTVKVVDELVKVMGRHKPENIVIEMARENQTTQKGQKNSRERMKRI

EEGIKELGSQILKEHPVENTQLQNEKLYLYYLQNGRDMYVDQELDINRL

SDYDVDHIVPQSFLKDDSIDNKVLTRSDKNRGKSDNVPSEEVVKKMKNY

WRQLLNAKLITQRKFDNLTKAERGGLSELDKAGFIKRQLVETRQITKHV

AQILDSRMNTKYDENDKLIREVKVITLKSKLVSDFRKDFQFYKVREINN

YHHAHDAYLNAVVGTALIKKYPKLESEFVYGDYKVYDVRKMIAKSEQEI

GKATAKYFFYSNIMNFFKTEITLANGEIRKRPLIETNGETGEIVWDKGR

DFATVRKVLSMPQVNIVKKTEVQTGGFSKESILPKRNSDKLIARKKDWD

PKKYGGFDSPTVAYSVLVVAKVEKGKSKKLKSVKELLGITIMERSSFEK

NPIDFLEAKGYKEVKKDLIIKLPKYSLFELENGRKRMLASAGELQKGNE

LALPSKYVNFLYLASHYEKLKGSPEDNEQKQLFVEQHKHYLDEIIEQIS

EFSKRVILADANLDKVLSAYNKHRDKPIREQAENIIHLFTLTNLGAPAA

FKYFDTTIDRKRYTSTKEVLDATLIHQSITGLYETRIDLSQLGGD
```

The CRISPR-Cas systems of bacteria and archaea confer acquired immunity by incorporating fragments of viral or plasmid DNA into CRISPR loci and utilizing the transcribed crRNAs to guide nucleases to degrade homologous sequences (Bhaya et al. Annual review of genetics 45:273-297 (2011); Wiedenheft et al. Nature 482:331-338 (2012)). In Type II CRISPR systems, a ternary complex of Cas9 nuclease with crRNA and tracrRNA (trans-activating crRNA) binds to and cleaves dsDNA protospacer sequences that match the crRNA spacer and also contain a short protospacer-adjacent motif (PAM) (Gasiunas et al. Proc. Natl. Acad. Sci. U.S.A. 109:E2579-2586 (2012); Jinek et al. Science 337:816-821 (2012)). Fusing the crRNA and tracrRNA produces a single guide RNA (sgRNA) that is sufficient to target Cas9 (Jinek, Supra).

According to one aspect, the RNA guided DNA binding protein includes homologs and orthologs of Cas9 which retain the ability of the protein to bind to the DNA, be guided by the RNA and cut the DNA. According to one aspect, the Cas9 protein includes the sequence as set forth for naturally occurring Cas9 from *S. pyogenes* and protein sequences having at least 30%, 40%, 50%, 60%, 70%, 80%, 90%, 95%, 98% or 99% homology thereto and being a DNA binding protein, such as an RNA guided DNA binding protein.

According to one aspect, an engineered Cas9-gRNA system is provided which enables RNA-guided genome cutting in a site specific manner, if desired, and modification of the genome by insertion of exogenous donor nucleic acids. The guide RNAs are complementary to target sites or target loci on the DNA. The guide RNAs can be crRNA-tracrRNA chimeras. The Cas9 binds at or near target genomic DNA. The one or more guide RNAs bind at or near target genomic DNA. The Cas9 cuts the target genomic DNA and exogenous donor DNA is inserted into the DNA at the cut site.

Accordingly, methods are directed to the use of a guide RNA with a Cas9 protein and an exogenous donor nucleic acid to multiplex insertions of exogenous donor nucleic acids into DNA within a cell expressing Cas9 by cycling the insertion of nucleic acid encoding the RNA and exogenous donor nucleic acid, expressing the RNA, co-localizing the RNA, Cas9 and DNA in a manner to cut the DNA, and insertion of the exogenous donor nucleic acid. The method steps can be cycled in any desired number to result in any desired number of DNA modifications. Methods of the present disclosure are accordingly directed to editing target genes using the Cas9 proteins and guide RNAs described herein to provide multiplex genetic and epigenetic engineering of cells.

Further aspects of the present disclosure are directed to the use of DNA binding proteins or systems in general for the multiplex insertion of exogenous donor nucleic acids into the DNA, such as genomic DNA, of a cell, such as a bacterial cell. One of skill in the art will readily identify exemplary DNA binding systems based on the present disclosure.

According to certain aspects of the disclosure, methods are provided for modulating the microbial population and/or the genetic makeup of an organism. As used herein, the term "organism" includes, but is not limited to, a human, a non-human primate, a cow, a horse, a sheep, a goat, a pig, a dog, a cat, a rabbit, a mouse, a rat, a gerbil, a frog, a toad, a fish (e.g., *D. rerio*) a roundworm (e.g., *C. elegans*) and any transgenic species thereof. The term "organism" further includes, but is not limited to, a yeast (e.g., *S. cerevisiae*) cell, a yeast tetrad, a yeast colony, a bacterium, a bacterial colony, a virion, virosome, virus-like particle and/or cultures thereof, and the like.

According to certain aspects of the disclosure, methods are provided for altering the microbiota of an ecological environment, e.g., an individual. As used herein, the term "microbiota" refers to the collective colonization of a subject by a vast number of microbes. The word microbiota represents an ensemble of microorganisms that resides in a previously established environment. Human beings have clusters of bacteria in different parts of the body, such as in the surface or deep layers of skin (skin microbiota), the mouth (oral microbiota), the vagina (vaginal microbiota), and so on. See *Nature* (2012) 492, entire issue, for a review of the human microbiota.

As used herein, the term "gut microbiota" or "gut flora" refers to the microbe population living in the digestive tract. It contains tens of trillions of microorganisms, including at least 1000 different species of known bacteria with more than 3 million genes (150 times more than human genes). Microbiota can, in total, weigh up to 2 kg. One third of the human gut microbiota is common to most people, while two thirds are specific to each one of us.

As used herein, the terms "microorganism" and "microbe" refer to tiny organisms. Most microorganisms and microbes are unicellular, although some multicellular organisms are microscopic, while some unicellular protists and bacteria (e.g., *T. namibiensis*) called are visible to the naked eye. Microorganisms and microbes include, but are not limited to, bacteria, fungi, archaea and protists, microscopic plants, and animals (e.g., plankton, the planarian, the amoeba) and the like.

Bacteria include, but are not limited to, gram positive bacteria, gram negative bacteria, acid-fast bacteria and the like.

As used herein, gram positive bacteria include, but are not limited to, *Actinomedurae, Actinomyces israelii, Bacillus anthracis, Bacillus cereus, Clostridium botulinum, Clostridium difficile, Clostridium perfringens, Clostridium tetani, Corynebacterium, Enterococcus faecalis, Listeria monocytogenes, Nocardia, Propionibacterium acnes, Staphylococcus aureus, Staphylococcus epiderm, Streptococcus mutans, Streptococcus pneumoniae* and the like.

As used herein, gram negative bacteria include, but are not limited to, *Afipia felis, Bacteroides, Bartonella bacilliformis, Bortadella pertussis, Borrelia burgdorferi, Borrelia recurrentis, Brucella, Calymmatobacterium granulomatis, Campylobacter, Escherichia coli, Francisella tularensis, Gardnerella vaginalis, Haemophilius aegyptius, Haemophilius ducreyi, Haemophilius influenziae, Heliobacter pylori, Legionella pneumophila, Leptospira interrogans, Neisseria meningitidia, Porphyromonas gingivalis, Providencia sturti, Pseudomonas aeruginosa, Salmonella enteridis, Salmonella typhi, Serratia marcescens, Shigella boydii, Streptobacillus moniliformis, Streptococcus pyogenes, Treponema pallidum, Vibrio cholerae, Yersinia enterocolitica, Yersinia pestis* and the like.

As used herein, acid-fast bacteria include, but are not limited to, *Myobacterium avium, Myobacterium leprae, Myobacterium tuberculosis* and the like.

As used herein, other bacteria not falling into the other three categories include, but are not limited to, *Bartonella henseiae, Chlamydia psittaci, Chlamydia trachomatis, Coxiella burnetii, Mycoplasma pneumoniae, Rickettsia akari, Rickettsia prowazekii, Rickettsia rickettsii, Rickettsia tsutsugamushi, Rickettsia typhi, Ureaplasma urealyticum, Diplococcus pneumoniae, Ehrlichia chafensis, Enterococcus faecium, Meningococci* and the like.

According to certain aspect of the invention, phages and their genetic material are provided. In other embodiments, one or more ribonucleic acid sequences is complementary to an exogenous phage nucleic acid sequence, e.g., a conserved nucleic acid sequence, is provided. As used herein, the terms "phage" and "bacteriophage" are used interchangeably. Phage can be distinguished from each another based on their genetic composition and/or their virion morphology. Some phage have double stranded DNA genomes, including phage of the corticoviridae, lipothrixviridae, plasmaviridae, myroviridae, siphoviridae, sulfolobus shibate, podoviridae, tectiviridae and fuselloviridae families. Other phage have single stranded DNA genomes, including phage of the microviridae and inoviridae families. Other phage have RNA genomes, including phage of the leviviridae and Cystoviridae families. Exemplary bacteriophage include, but are not limited to, Wphi, Mu, T1, T2, T3, T4, T5, T6, T7, P1, P2, P4, P22, fd, phi6, phi29, phiC31, phi80, phiX174, SP01, M13, MS2, PM2, SSV-1, L5, PRD1, Qbeta, lambda, UC-1, HK97, HK022 and the like.

As used herein, the term "conserved nucleic acid sequence" refers to a string of nucleotides in DNA or RNA that is similar across multiple species, strains and/or individuals. A known set of conserved sequences can be represented by a consensus sequence. In certain exemplary embodiments, a first nucleic acid sequence is conserved with respect to a second nucleic acid sequence if the two sequences share greater than 50%, greater than 55%, greater than 60%, greater than 65%, greater than 70%, greater than 75%, greater than 80%, greater than 85%, greater than 90%, greater than 91%, greater than 92%, greater than 93%, greater than 94%, greater than 95%, greater than 96%, greater than 97%, greater than 98%, or greater than 99% sequence identity.

In certain aspects of the invention, one or more ribonucleic acid sequences that is complementary to an exogenous virulence nucleic acid sequence is provided, e.g., a nucleic acid sequence that encodes a virulence factor. As used herein, a "virulence factor" refers to a molecule expressed and/or secreted by a pathogen (e.g., bacteria, viruses, fungi and/or protozoa). Virulence factors can mediate, e.g., 1) colonization of a niche in the host, 2) evasion of the host's immune response, 3) inhibition of the host's immune response, 4) entry into and exit out of cells, and/or 5) obtaining nutrition from the host.

Virulence factors can cause disease in a host by converting non-pathogenic bacteria into pathogenic bacteria. In bacteria, virulence factors are often encoded on mobile genetic elements, such as phages, and can easily be spread through horizontal gene transfer. Some bacteria, such as *E. coli* O157:H7, gain the majority of their virulence from mobile genetic elements.

As used herein, the term "mobile genetic element" refers to a type of DNA that can relocate within a genome, including, but not limited to, transposons (e.g., retrotransposons, DNA transposons, insertion sequences and the like), plasmids, phage elements (e.g., Mu), group II introns and the like. A database of mobile genetic elements suitable for use with the methods and compositions described herein can be found at the Worldwide Web Site aclme.ul.ac.be, incorporated herein by reference in its entirety for all purposes. See also, Miller, W. J.; Capy, P., eds. (2004), Mobile genetic elements: protocols and genomic applications, Humana Press, ISBN 1-58829-007-7, and Shapiro, J. A., ed. (1983), Mobile genetic elements, Academic Press, ISBN 0-12-638680-3.

Certain aspects of the invention pertain to vectors, such as, for example, expression vectors, containing a foreign nucleic acid sequence encoding a plurality of ribonucleic acid sequences. As used herein, the term "vector" refers to a nucleic acid sequence capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. By way of example, but not of limitation, a vector of the invention can be a single-copy or multi-copy vector, including, but not limited to, a BAC (bacterial artificial chromosome), a fosmid, a cosmid, a plasmid, a suicide plasmid, a shuttle vector, a P1 vector, an episome, YAC (yeast artificial chromosome), a bacteriophage or viral genome, or any other suitable vector. The host cells can be any cells, including prokaryotic or eukaryotic cells, in which the vector is able to replicate.

Certain vectors are capable of autonomous replication in a host cell into which they are introduced (e.g., bacterial vectors having a bacterial origin of replication and episomal mammalian vectors).

Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

In certain exemplary embodiments, an exogenous nucleic acid described herein is expressed in bacterial cells using a bacterial expression vector such as, e.g., a fosmid. A fosmid is a cloning vector that is based on the bacterial F-plasmid. The host bacteria will typically only contain one fosmid molecule, although an inducible high-copy ori can be included such that a higher copy number can be obtained (e.g., pCC1FOS™, pCC2FOS™). Fosmid libraries are particularly useful for constructing stable libraries from complex genomes. Fosmids and fosmid library production kits are commercially available (EPICENTRE® Biotechnologies, Madison, Wis.). For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In certain exemplary embodiments, the recombinant expression vectors comprise a nucleic acid sequence (e.g., a foreign nucleic acid sequence encoding a plurality of ribonucleic acid sequences) in a form suitable for expression of the nucleic acid sequence in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the foreign nucleic acid sequence encoding a plurality of ribonucleic acid sequences described herein is linked to the regulatory sequence(s) in a manner which allows for expression of the nucleic acid sequence. The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). It will be appreciated by those skilled in the art that the design of the expression vector can depend on such factors as the choice of the host cell to be transformed, the level of expression of protein desired, and the like.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, insect cells, fungal cells, archaeal cells, eubacterial cells and the like. Cells include eukaryotic cells such as yeast cells, plant cells, and animal cells. Particular cells include mammalian cells. Other suitable cells are known to those skilled in the art.

Target nucleic acids include any nucleic acid sequence to which a co-localization complex as described herein can be useful to nick or cut. Target nucleic acids include genes. For purposes of the present disclosure, DNA, such as double stranded DNA, can include the target nucleic acid and a co-localization complex can bind to or otherwise co-localize with the DNA at or adjacent or near the target nucleic acid and in a manner in which the co-localization complex may have a desired effect on the target nucleic acid. Such target nucleic acids can include endogenous (or naturally occurring) nucleic acids and exogenous (or foreign) nucleic acids. One of skill based on the present disclosure will readily be able to identify or design guide RNAs and Cas9 proteins which co-localize to a DNA including a target nucleic acid. One of skill will further be able to identify transcriptional regulator proteins or domains which likewise co-localize to a DNA including a target nucleic acid. DNA includes genomic DNA, mitochondrial DNA, viral DNA or exogenous DNA. According to one aspect, materials and methods useful in the practice of the present disclosure include those described in Di Carlo, et al., *Nucleic Acids Research,* 2013, vol. 41, No. 7 4336-4343 hereby incorporated by reference in its entirety for all purposes including exemplary strains and media, plasmid construction, transformation of plasmids, electroporation of transient gRNA cassette and donor nucleic acids, transformation of gRNA plasmid with donor DNA into Cas9-expressing cells, galactose induction of Cas9, identification of CRISPR-Cas targets in yeast genome, etc. Additional references including information, materials and methods useful to one of skill in carrying out the invention are provided in Mali et al. Science 2013 February; 339(6121):823-826; Storici et al. PNAS 2003 100:14994-14999; and Jinek et al. Science 2012 337:816-821 each of which are hereby incorporated by reference in their entireties for all purposes.

Foreign nucleic acids (i.e., those which are not part of a cell's natural nucleic acid composition) may be introduced into a cell using any method known to those skilled in the art for such introduction. Such methods include transfection, transduction, infection (e.g., viral transduction), injection, microinjection, gene gun, nucleofection, nanoparticle bombardment, transformation, conjugation, by application of the nucleic acid in a gel, oil, or cream, by electroporation, using lipid-based transfection reagents, or by any other suitable transfection method. One of skill in the art will readily understand and adapt such methods using readily identifiable literature sources.

As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI™ (Polyplus-transfection Inc., New York, N.Y.), EFFECTENE® (Qiagen, Valencia, Calif.), DREAMFECT™ (OZ Biosciences, France) and the like), or electroporation (e.g., in vivo electroporation). Suitable methods for transforming or transfecting host cells can be found in Sambrook, et al. (*Molecular Cloning: A Laboratory Manual.* 2nd, ed., Cold Spring harbor Laboratory, Cold Spring Harbor Laboratory Press, Cold Spring Harbor, N.Y., 1989), and other laboratory manuals.

In certain aspects a cell (e.g., a bacterial cell) or a nucleic acid sequence described herein can be incorporated into pharmaceutical compositions suitable for administration. Such compositions typically comprise the nucleic acid molecule or protein and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In certain exemplary embodiments, a pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the candidate or test compound(s) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: A binder such as microcrystalline cellulose, gum tragacanth or gelatin; an excipient such as starch or lactose, a disintegrating agent such as alginic, acid, Primogel, or corn starch; a lubricant such as magnesium stearate or Sterotes; a glidant: such as colloidal silicon dioxide; a sweetening agent such as sucrose or saccharin; or a flavoring agent such as peppermint, methyl salicylate, or orange flavoring.

In one embodiment, a cell (e.g., a bacterial cell) or a nucleic acid sequence is prepared with carriers that will protect the cell (e.g., bacterial cell) or nucleic acid sequence against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

Nasal compositions generally include nasal sprays and inhalants. Nasal sprays and inhalants can contain one or more active components and excipients such as preservatives, viscosity modifiers, emulsifiers, buffering agents and the like. Nasal sprays may be applied to the nasal cavity for local and/or systemic use. Nasal sprays may be dispensed by a non-pressurized dispenser suitable for delivery of a metered dose of the active component. Nasal inhalants are intended for delivery to the lungs by oral inhalation for local and/or systemic use. Nasal inhalants may be dispensed by a closed container system for delivery of a metered dose of one or more active components.

In one embodiment, nasal inhalants are used with an aerosol. This is accomplished by preparing an aqueous aerosol, liposomal preparation or solid particles containing the compound. A non-aqueous (e.g., fluorocarbon propellant) suspension could be used. Sonic nebulizers may be used to minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The cell (e.g., a bacterial cell) or a nucleic acid sequence can also be prepared in the form of suppositories (e.g., with conventional suppository bases such as cocoa butter and other glycerides) or retention enemas for rectal delivery.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of candidate or test compound(s) can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from cell culture assays and/or animal studies can be used in formulating a range of dosage for use in humans. The dosage typically will lie within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In certain exemplary embodiments, a method for treatment of infection by a microorganism includes the step of administering a therapeutically effective amount of an agent (e.g., one or more candidate or test compounds) which modulates (e.g., kills and/or inhibits the growth of), one or more microorganisms to a subject. As defined herein, a therapeutically effective amount of agent (i.e., an effective dosage) ranges from about 0.001 to 30 mg/kg body weight, from about 0.01 to 25 mg/kg body weight, from about 0.1 to 20 mg/kg body weight, or from about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an inhibitor can include a single treatment or, in certain exemplary embodiments, can include a series of treatments. It will also be appreciated that the effective dosage of inhibitor used for treatment may increase or decrease over the course of a particular treatment. Changes in dosage may result from the results of diagnostic assays as described herein. The pharmaceutical compositions can be included in a container, pack, or dispenser together with instructions for administration.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures and accompanying claims.

Example I

Overview

Native bacteria are depleted with phages to benefit strains having Cas9-mediated phage immunity. This highly novel ecological approach creates a competitive advantage for Cas9-immunized cells proportional to the amount of phage added to the diet.

Placing Cas9 cassettes on mobile elements that spread from cell to cell can decrease the incidence of Cas9-targeted genes in native bacteria. Rather than just using Cas9 to kill pathogens as previously suggested (Bikard et al. Cell Host Microbe 2012 August; 12(2):177-186), natives can be permanently immunized using a novel method described herein that copies Cas9 immunity cassettes into the bacterial chromosome. Recipients are optionally engineered to express other genes placed in the cassette.

Importantly, Cas9-mediated immunization is evolutionarily stable. Targeting many sequences within a gene removes the possibility of mutational escape by eliminating the benefit conferred by single or even multiple mutations, while mixing spacers targeting phages with spacers targeting pathogenic genes prevents cells from keeping one immunity while discarding the other.

These highly innovative ecological approaches provide the foundation for a new microbiota-centric paradigm for the promotion of human health. By developing tools to precisely sculpt the cellular and genetic composition of our internal ecosystems, microbial passengers are transformed into a second line of defense that is immunized against pathogenicity, resists dysbiosis, and responds to acute or chronic host illness by releasing therapeutic molecules in a controlled manner.

Figure 2:
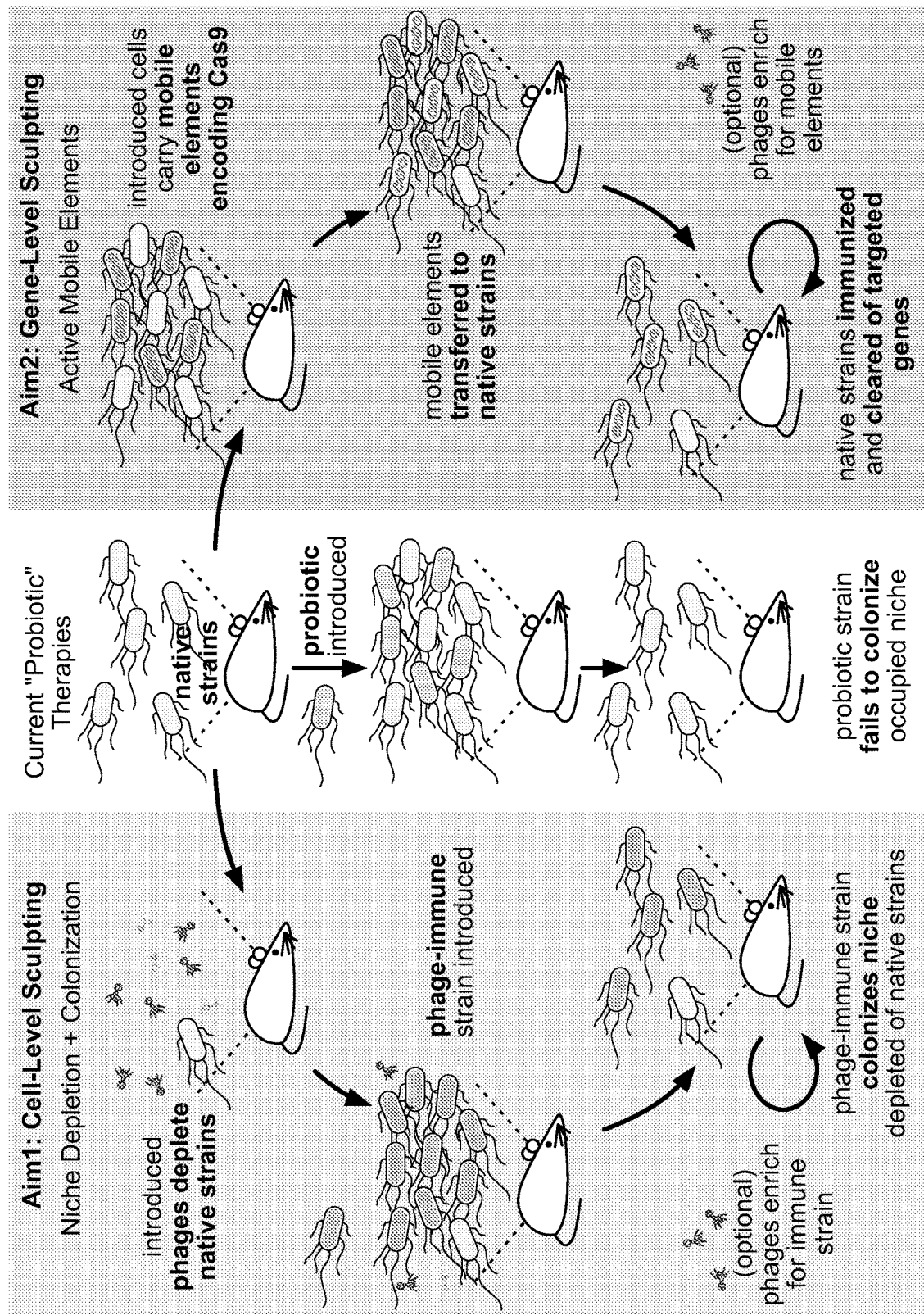
FIG. 2 schematically depicts methods to sculpt the cellular and genetic composition of the gut microbiota.

The Cas9-based methods described herein can be used to alter the composition of the microbiota within animal models. *E. coli* strains already resident in the murine gut are stabilized with an engineered phage-immune strain that gains a competitive advantage in the presence of phages (FIG. 2, left). The most advantageous methods of spreading mobile genetic elements encoding Cas9 immunity through resident bacteria are determined (FIG. 2, right). The techniques described above are used to alter the mouse microbiota to better resist infection by pathogenic bacteria encoding Shiga toxins. Whether stably colonized bacteria can secrete consistent and therapeutically useful levels of effector molecules in a mouse can be assayed for various effectors.

Individually housed mice are used to prevent copraphagic sharing of gut microbes. Mice are randomly allocated into experimental groups and the results are evaluated blindly (Muhlhausler et al. PLoS Biol. 2013; 11(2):e1001481) with the assistance of the animal facility staff. Because all experiments involve altering microbial fitness, sometimes in ways that can be transmitted to other cells, appropriate microbiological safety precautions are taken.

Example II

Replacing Resident Gut Bacteria by Adding Phages to the Diet, then Introducing Replacement Strains Granted Immunity to Phages with Cas 9

Phage-Mediated Depletion Will Allow Phage-Immune Species to Colonize

According to Freter's nutrient-niche hypothesis, migrants invading an established community typically fail to colonize because established residents are already consuming all available nutrients (Freter et al. Infect. Immun. 1983 February; 39(2):676-685), forcing some pathogens to induce inflammation to access alternative sources (Winter et al. Nature 2010 September; 467(7314):426-429). When microbial communities are disrupted by antibiotics, colonization rates increase (Lee et al. Nature 2013 September; 501(7467): 426-429) and peak with free sugar levels (Ng et al. Nature 2013 September). Invading pathogens can be blocked (Maltby et al. PLoS ONE 2013; 8(1):e53957 and Kamada et al. Science 2012 June; 336(6086):1325-1329) or cleared (Lawley et al. PLoS Pathog. 2012; 8(10):e1002995) by reintroducing groups of resident strains chosen for their ability to consume all of the nutrients preferred by the pathogen. Without intending to be bound by scientific theory, depleting a resident species with bacteriophages will vacate its nutritional niche and allow related phage-immunebacteriatocolonize.

Phage Presence can Determine which Strain Colonizes a Niche

Figure 3A:
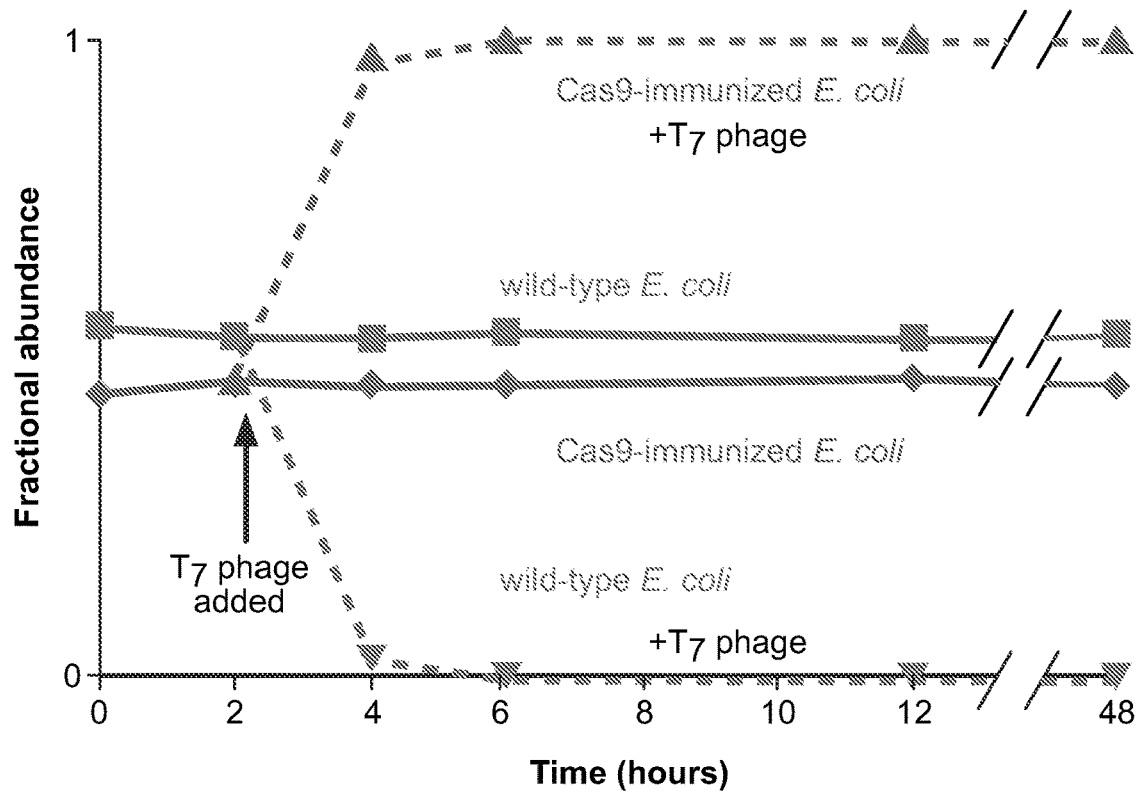
FIGS. 3A-3B graphically depict Cas9-mediated phage immunity Providing a strain with immunity and then adding phages allows it to dominate its cultures over a susceptible strain (top) without affecting other species (*Vibrio*, bottom).
Figure 3B:
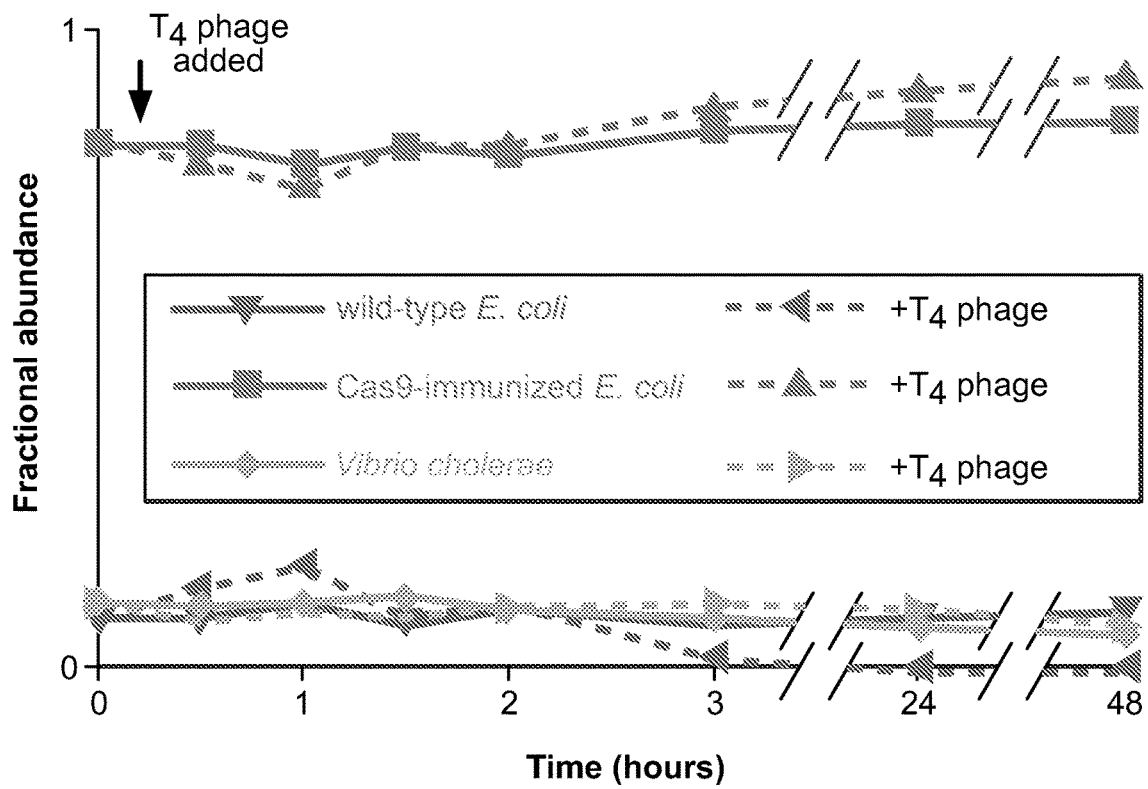

It was demonstrated that the strategy described herein is effective in laboratory culture. Cas9-mediated phage immunity incurs minimal fitness costs and allows immune strains to dominate susceptible competitors when phages are added (FIG. 3). High-activity spacers targeting highly conserved regions of the T4 and T7 phages were used, providing a ready-made cocktail of related phages that were chosen for their ability to target a wide range of *E. coli* strains (Kutter E. Methods Mol. Biol. 2009; 501:141-149 and Qimron et al. Proc. Natl. Acad. Sci. U.S.A. 2006 December; 103(50): 19039-19044).

A similar strategy was recently discovered in nature: the production of temperate bacteriophages by a naturally lysogenized strain of *E. faecalis* assists that strain in establishing and maintaining dominance of its intestinal niche in competition with nutritional competitors that are susceptible to the phage (Duerkop et al. Proc. Natl. Acad. Sci. U.S.A. 2012 October; 109(43):17621-17626). A mixture of only four phages chosen for their high strain specificity could reduce the total *E. coli* concentration in the gut by 60% (Chibani-Chennoufi et al. Antimicrob. Agents Chemother. 2004 July; 48(7):2558-2569) indicating that the broader-host-range cocktail described herein will deplete most strains of *E. coli* in the gut.

Replacing Native *E. coli* by Depleting with Phages and Recolonizing

The fraction of cells that can be replaced is measured, whether replacement is stable over time is determined, and whether periodic phage supplementation is needed to maintain the introduced strain is determined. To accomplish this, phages are added to the drinking water of C57/BL6 mice and the mice are orally dosed with a fluorescently labeled *E. coli* strain that was engineered to be immune to these phages using Cas9. The relative abundance of fluorescent cells are measured over time by plating fecal samples each day on MacConkey lactose plates, which select for the growth all *E. coli* cells (Macconkey A. J Hyg (Lond) 1905 July; 5(3):333-379). A second experimental group receives additional doses of phage each week, while control groups do not receive phages.

This experiment is run on two sets of mice. The first group is be "standardized" by treatment with streptomycin to preferentially eliminate facultative anaerobes such as *E. coli* and its competitors (Myhal et al. Eur. J. Clin. Microbiol. 1982 June; 1(3):186-192, then colonized with strep-resistant strains that are susceptible to the phages described herein. The second group of mice harbors native mouse *E. coli* strains. Without intending to be bound by scientific theory, it is expected that slightly lower rates of replacement in these mice occurs due to a handful of native strains that will not be susceptible to any of the phages. If replacement falls by half or more for this set, individual colonies are tested for phage susceptibility and new phages are added to the cocktail to improve depletion.

Minimizing Factors that could Limit Phage-Mediated Depletion

Phage-susceptible bacteria sometimes resist infection if they are in stationary or "persister" phase. Without intending to be bound by scientific theory, it is hypothesized that delivering phages with a nutrient source will induce cells to enter exponential phase and become vulnerable to phages. To test this hypothesis, experimental mice are given drinking water with phages and 2% gluconate and arabinose, two sugars that are preferentially utilized by *E. coli* strains but poorly absorbed by animals (Krog-Mikkelsen et al. Am. J. Clin. Nutr. 2011 August; 94(2):472-478). These sugars may be altered to those preferred by a targeted bacterial population.

Resident cells might resist phage depletion due to physical isolation within crypts, mucus, or lesions. Because most such pockets should open and close, it is anticipated that increased replacement levels in mice receiving repeated phage doses are observed. The GI tracts of the mice are dissected at the end of the experiment and tissue imaging is performed to identify the locations of fluorescent cells. Exemplary replacement rates include 20%, 50% and 80%.

In summary, this strategy has been determined to be effective in vitro. The most effective protocol for replacing resident *E. coli* strains in mice is determined with engineered phage-immune equivalents by optimizing phage dosing and nutrient availability while quantifying the number of labeled phage-immune cells. Due to the ease of conferring resistance to any phage whose genome sequence is known by targeting Cas9 to cleave sites in the phage genome, the method may be extended to any bacterial population with identified phages.

Example III

Methods of Spreading Cas9 Mobile Elements Through Bacteria in the Gut

Adding Many Effective Donor Cells is Key to Spreading Cas9 Immunization

Conjugation in the gut is most efficient when the concentration of host bacteria is high (Stecher et al. Proc. Natl. Acad. Sci. U.S.A. 2012 January; 109(4):1269-1274) and at least some of the cells are particularly effective as donors (Dionisio et al. Genetics 2002 December; 162(4):1525-1532). Without intending to be bound by scientific theory, it is hypothesized that orally delivering large numbers of highly efficient donor cells will enable transfer of conjugative plasmids encoding Cas9-based immunization to most targeted naïve cells within the microbiota.

Immunization Using Mobile Elements is Effective in the Laboratory

Figure 4:
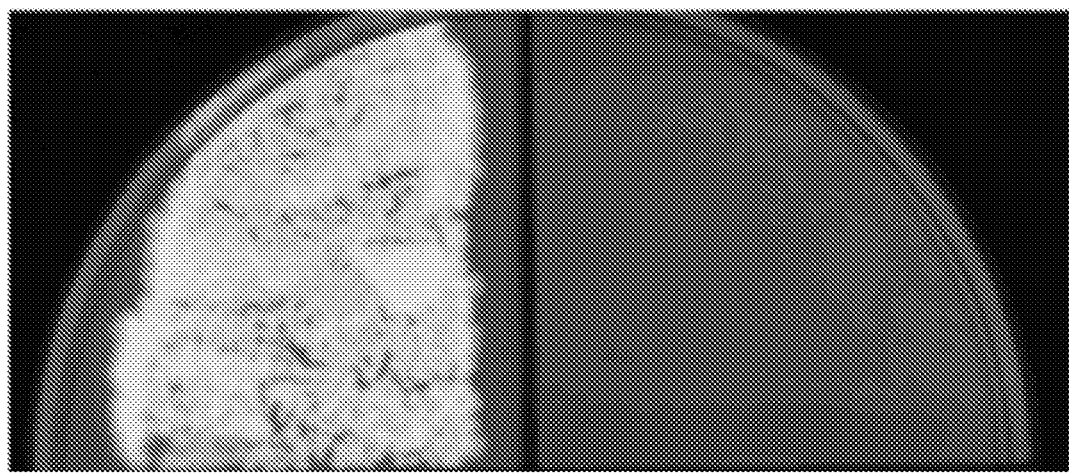
FIG. 4 depicts a bacterial plate showing that a conjugative plasmid encoding a Cas9 immunity cassette mixed with cells containing a targeted gene can eliminate the gene from the population as the conjugative plasmid spreads. The targeted gene encoding yellow fluorescent protein is eliminated from cells that acquire the Cas9 plasmid. (right side of plate).
Figure 5:
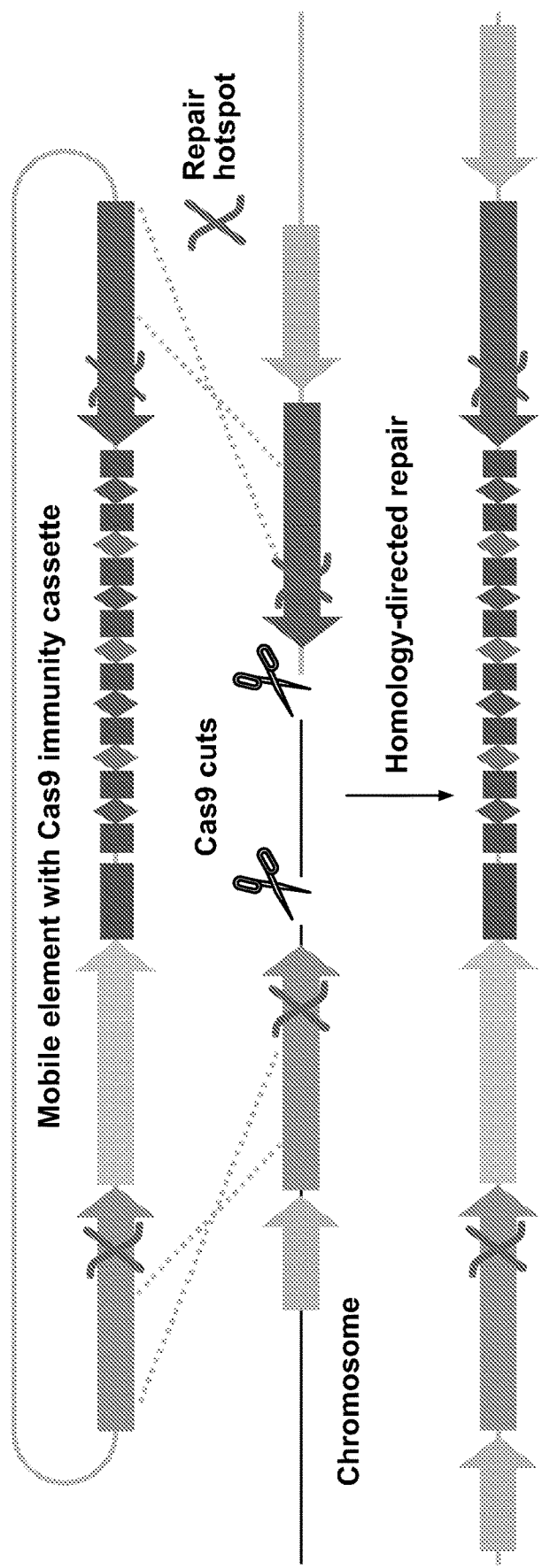
FIG. 5 schematically depicts a strategy for making a Cas9 cassette that copies itself into the genome. Cas9 mediates cuts between chromosomal repair hotspots in a target bacterial genome in order to integrate a Cas9 immunity cassette into the bacterial genome.
Figure 7:
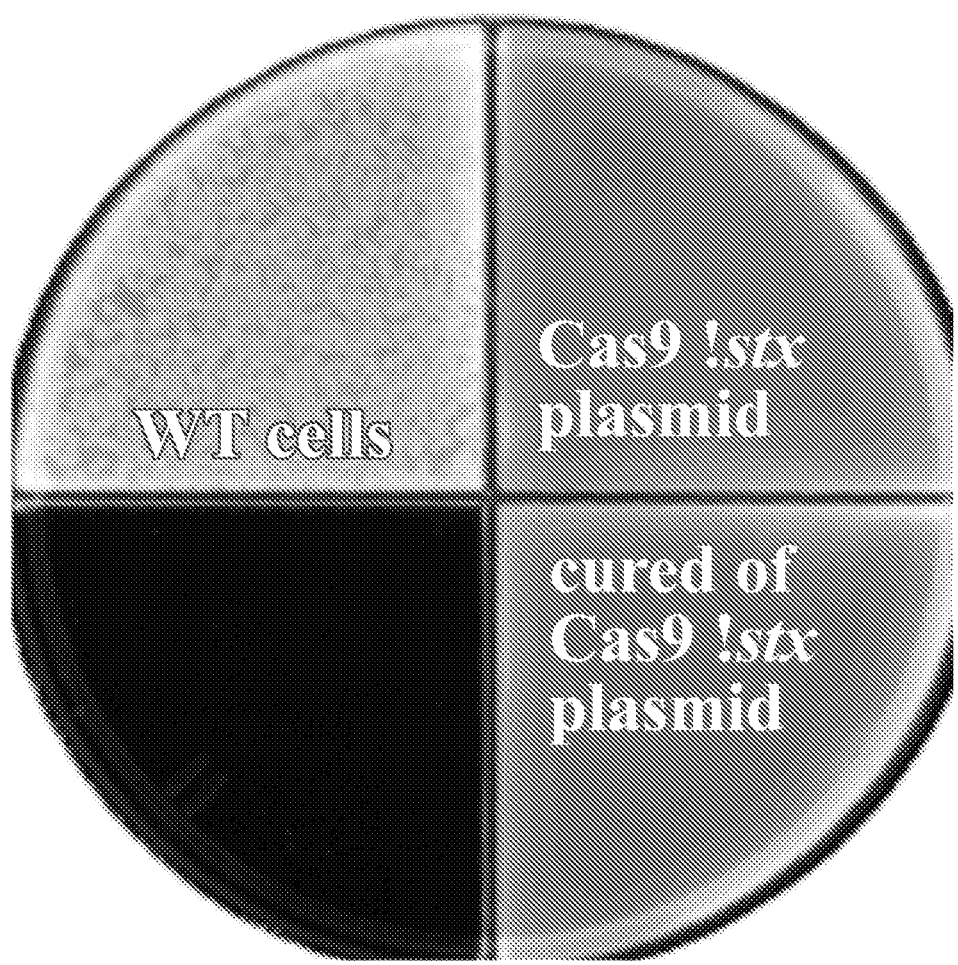
FIG. 7 depicts a bacterial plate showing that cured cells transformed with stx vector yielded no colonies because the !stx immunity cassette copied itself into the genome, showing the success of the strategy set forth in FIG. 6. Normal cells were readily transformed with a plasmid containing a targeted gene (top left). Cells with a Cas9-encoding plasmid targeting that gene could not be transformed with the plasmid (top right). When the cells were cured of the plasmid, they still could not be transformed due to a copy of Cas9 that remained in the genome (bottom right).
Figure 8:
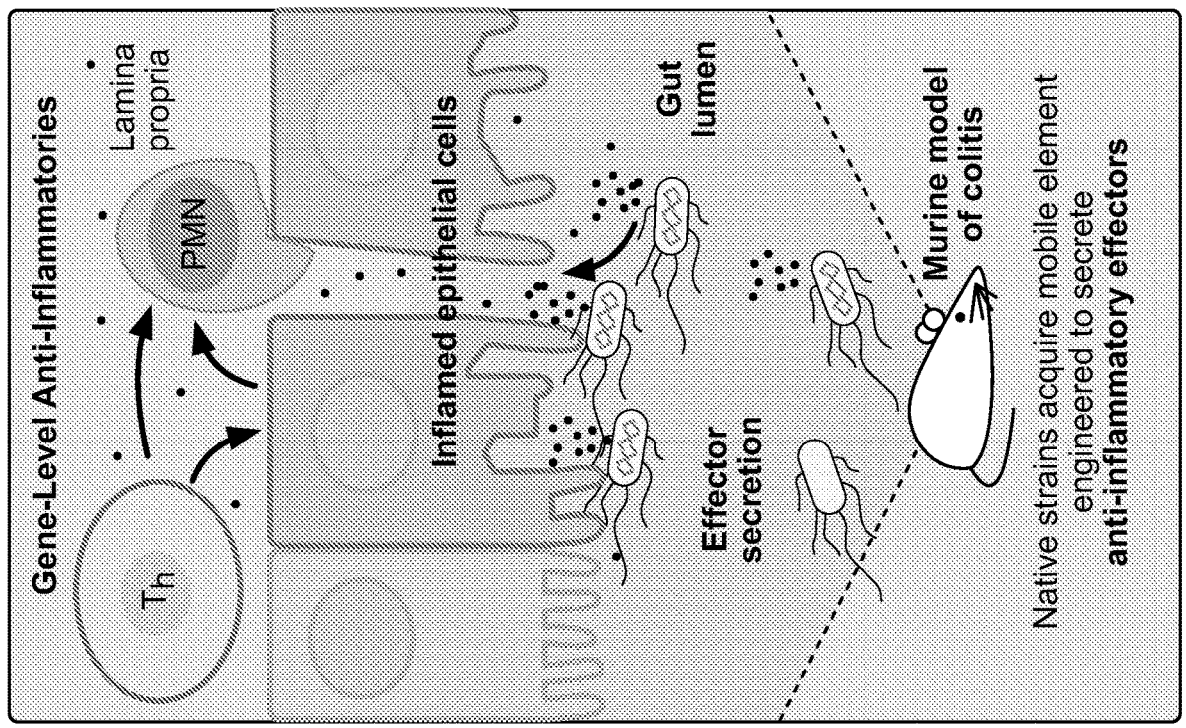
FIG. 8 schematically depicts stably colonized strains having improved in situ therapeutic effects over equivalent bacterial strains that do not stably colonize.
Figure 8:
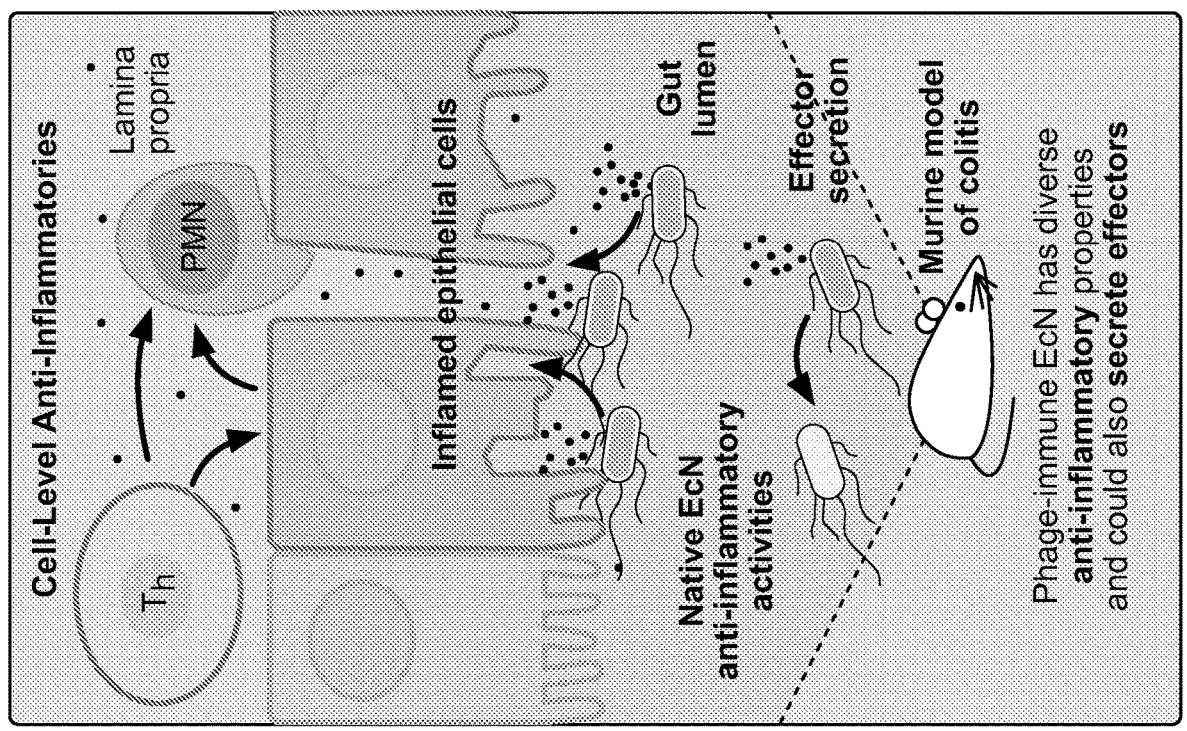

Conjugative plasmids encoding Cas9 immunity cassettes have been constructed. When conjugated into a recipient cell encoding a targeted gene, these immunity plasmids eliminated that gene with near-perfect reliability (FIG. 4). To ensure that cells are still immunized even if they subsequently lose the plasmid, a way was devised to make the Cas9 cassette efficiently copy itself into a highly conserved site on the *E. coli* chromosome. It does this by repeatedly cutting sites between repair hotspots (Cheng et al. J. Mol. Biol. 1984 December; 180(2):371-377) with Cas9 until homology-directed repair enzymes use the homologous sequences flanking the cassette copy it in place of the target sequence (FIG. 5). Cells that acquire and then lose an immunity plasmid still exhibit Cas9-mediated immunity to targeted genes due to the chromosomal copy (FIG. 7). Using this method, stable immunization of any cell accessible to conjugative plasmids carrying Cas9 can be achieved.

Bacterial "Blooms" Causing Efficient Conjugation can be Replicated In Vivo

Enterobacterial blooms of approximately $10^9$ *E. coli* per gram of feces result in plasmid transfer to nearly 100% of cells after several days (Stecher et al. Proc. Natl. Acad. Sci. U.S.A. 2012 January; 109(4):1269-1274). Because mice can be supplied with $10^9$ bacteria/mL drinking water (Vidal et al.

J. Clin. Microbiol. 2010 July; 48(7):2595-2598), bloom-level conjugation should be experimentally induced for an extended period.

Optimizing Transfer in Mice Using Fluorescent Plasmids

The fraction of *E. coli* in the murine gut that are accessible to fluorescently labeled F and R100 conjugative plasmids is determined (Anthony et al. J. Bacteriol. 1999 September; 181(17):5149-5159).

Donor bacteria and native *E. coli* are distinguished from one another by using a lacZ⁻ galK⁻ donor strain that was constructed which forms white instead of red colonies on MacConkey lactose+galactose plates. Counting fluorescent versus non-fluorescent red cells will quantify the fraction of *E. coli* that have acquired a plasmid.

To determine whether the method of copying Cas9 cassettes into the chromosome increases stability, mice are provided with drinking water containing $10^9$ donor bacteria/mL. Experimental groups 1 and 2 receive donors with copying and non-copying plasmids, while the control group receives donor cells without conjugative plasmids. Fecal samples from these mice are plated daily for ten weeks. At the end of the experiment, mice are sacrificed and subjected to tissue imaging to identify the physical locations of plasmid-containing cells.

Overcoming Barriers Preventing Conjugation

Physical barriers preventing donor cells from contacting recipients could block transfer. Since these barriers are likely transient, one experimental group is supplied with a new batch of donor cells every week and whether the fraction of modified native cells increases is observed.

Molecular barriers such as exclusion by related plasmids could also impede transfer (Achtman et al. Proc. Natl. Acad. Sci. U.S.A. 1977 November; 74(11):5104-5108). Compatible F and R100 conjugative plasmids (Willetts et al. J. Bacteriol. 1972 June; 110(3):843-851) are used, each of which is engineered to assist its partner by eliminating its respective wild-type competitor with Cas9. Whether these plasmids can overcome exclusion is determined by testing them in streptomycin-treated mice standardized with *E. coli* strains that universally contain wild-type competitors.

It is important to note that the success of Example III is independent of Example II. However, an optional combined approach uses phages to drive the spread of Cas9-containing mobile elements. This approach is tested by inserting spacers conferring phage immunity into the conjugative plasmids and supplementing the diet with phages to eliminate cells that have not yet acquired them.

Should the conjugative plasmid approach fail for unanticipated reasons, temperate phages that integrate into host cell genomes represent alternative delivery vehicles. Over 30% of *E. coli* contain at least one P2-like prophage (Odegrip et al. J. Bacteriol. 2006 February; 188(4):1643-1647), indicating that it is a highly successful vehicle for invading the genomes of enterobacteria.

Native cell acquisition rates of 20% is considered a qualified success, 50% is considered a moderate success, and 80% is considered an outstanding success.

In summary, the most effective protocol for stably incorporating Cas9 immunity cassettes into resident bacteria is determined using mobile genetic elements as delivery vehicles.

Example IV

Altering the Microbiota to Resist Toxin-Producing Pathogens

Harnessing Colonization Resistance and Immunization for Therapeutics

Protective strains within the microbiota can prevent invading pathogens from provoking inflammation and dysbiosis. The Nissle 1917 EcN strain of *E. coli* was isolated from a soldier who was apparently immune to dysentery (Nissle et al. Med Klin 1918; 2:29-30). It has a long history of safe use in humans (Schultz et al. Practical Gastroenterology 2010 March; 11-19) and is highly antagonistic towards pathogenic enterobacteria (Rund et al. Int. J. Med. Microbiol. 2013 January; 303(1):1-8), but like all probiotics, does not stably colonize the gut (Prilassnig et al. Wien. Klin. Wochenschr. 2007; 119(15-16):456-462). Using phages and Cas9 to stably render EcN the dominant *E. coli* strain in the gut could confer equivalent immunity.

Figure 6:
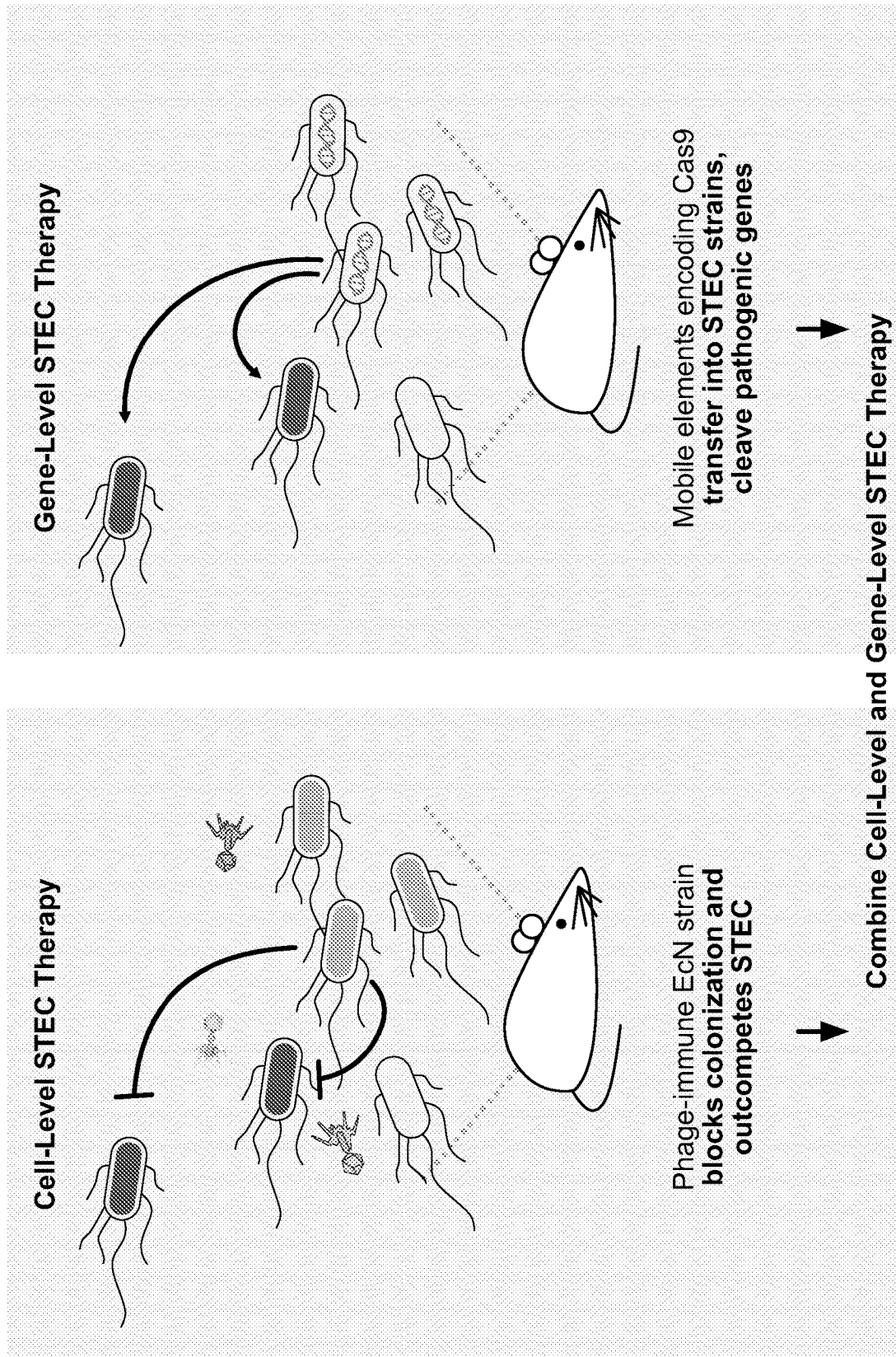
FIG. 6 schematically depicts that Cas9 immunity cassettes delivered to Shiga toxin-producing *E. coli* (STEC) strains such as EDL933 can render them harmless by cleaving the toxin-encoding genes, while depleting native bacteria using phages and replacing them with protective strains such as EcN that have been immunized against those phages with Cas9 can prevent the growth of STEC strains.

Alternatively, delivering Cas9 could directly eliminate pathogenic genes. Cas9 immunity cassettes delivered to Shiga toxin-producing *E. coli* (STEC) strains such as EDL933 can render them harmless by cleaving the toxin-encoding genes (FIG. 6).

Building Phage-Immune EcN and Genome-Copying Anti-Stx Plasmids

Phage-immune EcN strains suitable for colonizing mice have been constructed. Streptomycin-treated mice colonized with EcN are known to resist subsequent colonization by STEC, indicating that methods presented herein are viable (Leatham et al. Infect. Immun. 2009 July; 77(7):2876-2886; Maltby et al. PLoS ONE 2013; 8(1):e53957).

Similarly, plasmids carrying a Cas9 immunity cassette targeting both stx1 and stx2 that also copies itself into the genome were constructed. Crucially, cells remained immune to stx after being cured of the plasmid, demonstrated by their continued inability to be transformed with a vector carrying a truncated stx cassette (FIG. 7).

Measuring the Efficacy of Phage-Immune EcN Against STEC Colonization in Streptomycin-Treated Mice The streptomycin-treated mouse is an excellent small animal model of STEC colonization (Mohawk et al. J. Biomed. Biotechnol. 2011; 2011:258185; Law et al. Cold Spring Harb Perspect Med 2013 March; 3(3):a00997775, 76). Moreover, *E. coli* strains can be ensured to be the dominant facultative anaerobes in these mice—as is the case in humans (Tenaillon et al. Nat. Rev. Microbiol. 2010 March; 8(3):207-217)—by colonizing them with strep-resistant mutants of their own native *E. coli* strains. Relative abundance using strains is quantified with different resistance markers (Maltby et al. PLoS ONE 2013; 8(1):e53957; Miranda et al. Infect. Immun. 2004 March; 72(3): 1666-1676).

To evaluate EcN as a prophylactic, the mice are colonized with phage-immune EcN according to the protocol determined in Example II and challenge them with O157:H7 STEC one week later. To evaluate phage-immune EcN as a treatment for active STEC infection, mice are given EDL933 in their drinking water followed by phages and then phage-immune EcN the next day.

Deploying Cas9 Mobile Elements to Cleave Stx Genes in Mice

BALB/c mice exposed to high levels of EDL933 exhibit stx-dependent weight loss and occasionally renal failure and death, an outcome analogous to the hemolytic-uremic syndrome observed in some human STEC patients (Mohawk et al. Microb. Pathog. 2010 April; 48(3-4):131-142). To determine whether Cas9 mobile elements targeting stx are a viable treatment for STEC toxicity, mice are given drinking water containing a conjugative plasmid targeting stx1 and stx2 1 or 3 days after intragastric EDL933 delivery. A second experimental group uses phage-immune EcN as the donor strain for the mobile element and administer phages before mobile element introduction, thereby combining the advantages of cellular and gene-level therapy. Control groups receive Cas9 immunity cassettes that do not target the toxin-encoding genes. Fecal samples are plated daily and mice evaluated for weight gain and mortality over 2 weeks.

Adjusting Strains and Phages as Needed

As with humans, the native microbiota of some mice may block EDL933 colonization. If EDL933 colonization fails in all mice, animals may first be colonized with human *E. coli* isolates rendered resistant to streptomycin, which may prove more susceptible to invasion.

EcN is known to block EDL933 colonization more efficiently when combined with another strain with different nutrient requirements (Maltby et al. PLoS ONE 2013; 8(1): e53957). Therefore, a second experimental group colonized with phage-immune EcN and the related commensal strain HS is tested.

At least one of the lytic phages in the starting cocktail can lyse many STEC strains (Goodridge et al. Appl. Environ. Microbiol. 2003 September; 69(9):5364-5371), which is likely to be beneficial to the mice unless it causes prophage induction and stx production, in which case those phages are omitted from the cocktail.

Prophylaxis or treatment is considered effective if STEC levels are prevented from rising in streptomycin-treated mice or weight loss and mortality rates by are reduced by >50% in conventional mice. Success leads to follow-up experiments against other strains of STEC, such as the 0104:H4 strain responsible for the outbreak in Germany in 2011 (Rasko et al. N. Engl. J. Med. 2011 August; 365(8): 709-717), as well as strains of *Salmonella* (Deriu et al. Cell Host Microbe 2013 July; 14(1):26-37).

In summary, the efficacy of phage-assisted EcN colonization and mobile elements carrying Cas9 for the prevention and treatment of Shiga toxin-producing *E. coli* infection in mice is measured.

Example V

Validation of Methods of Producing Stable Levels of Therapeutic Effectors In Situ

Maintaining Consistent Levels of Therapeutics In Situ

Effector molecules produced in situ by transiently delivered bacteria are more therapeutically effective than much higher doses (>1,000-fold) of the purified effector (Vandenbroucke et al. Gastroenterology 2004 August; 127(2):502-513), likely due to the close proximity of the bacteria and responsive cells in the epithelium. Meanwhile, germ-free mice mono-colonized by protective bacteria are much more resistant to colitis than conventional mice fed the same strain (Hudcovic et al. Folia Microbiol. (Praha) 2007; 52(6):618-626). Without intending to be bound by scientific theory, it is thought that that stably colonized bacteria will be more effective than transiently delivered strains due to more sustained epithelial contact and more consistent delivery of secreted effectors (Steidler et al. Nat. Biotechnol. 2003 July; 21(7):785-789; Su et al. Lett. Appl. Microbiol. 2007 February; 44(2):120-125).

Scientifically, stably colonized bacteria can be used to directly test hypotheses concerning the roles of various effectors in host functions. Therapeutically, in situ secretion of one or many effectors could treat metabolic, immune, or other enteric disorders with fewer systemic side effects (Vandenbroucke et al. Mucosal Immunol 2010 January; 3(1):49-56).

In certain aspects, the methods developed in Example II can be used to stably replace native bacteria with a protective strain such as EcN, which could be further engineered to secrete therapeutic effectors. In other aspects, native bacteria could be modified to secrete effectors using the methods of Example III.

The methods and compositions described herein could lead to treatments for inflammatory disorders linked to the gut microbiota, including inflammatory bowel disease (IBD) (Kamada et al. Nat. Immunol. 2013 July; 14(7):685-690; Horwitz B. Inflamm. Bowel Dis. 2007 April; 13(4):490-500; Abraham et al. N. Engl. J. Med. 2009 November; 361(21): 2066-2078; Manichanh et al. Nat Rev Gastroenterol Hepatol 2012 October; 9(10):599-608; DuPont et al. Nat Rev Gastroenterol Hepatol 2011 September; 8(9):523-531; Nell et al. Nat. Rev. Microbiol. 2010 August; 8(8):564-577) and irritable bowel syndrome (IBS) (Camilleri et al. N. Engl. J. Med. 2012 October; 367(17):1626-1635; Othman et al. Curr. Opin. Gastroenterol. 2008 January; 24(1):11-16; Salonen et al. Microbiology (Reading, Engl.) 2010 November; 156(Pt 11):3205-3215; Parkes et al. Am. J. Gastroenterol. 2008 June; 103(6):1557-1567). Priority effector targets include the IL-23R pathway (Abraham et al. Annu. Rev. Med. 2009; 60:97-110; Ahern et al. Immunity 2010 August; 33(2):279-288; Buonocore et al. Nature 2010 April; 464(7293):1371-1375; Sarra et al. Inflamm. Bowel Dis. 2010 October; 16(10):1808-1813), NOD2 (Ogura et al. Nature 2001 May; 411(6837):603-606; Hugot et al. Nature 2001 May; 411 (6837):599-603; Inohara et al. J. Biol. Chem. 2003 February; 278(8):5509-5512; Travassos et al. Nat. Immunol 2010 January; 11(1):55-62; Petnicki-Ocwieja et al. Proc. Natl. Acad. Sci. U.S.A. 2009 September; 106(37):15813-15818; Hedl et al. Proc. Natl. Acad. Sci. U.S.A. 2007 December; 104(49):19440-19445), and Paneth cells (Murphy et al. Curr Gastroenterol Rep 2012 April; 14(2):146-152; Bevins et al. Nat. Rev. Microbiol. 2011 May; 9(5):356-368; Ogura et al. Gut 2003 November; 52(11):1591-1597; Welz et al. Nature 2011 September; 477(7364):330-334), but any molecule identified as anti-inflammatory or cytoprotective could be a suitable effector. Candidates include, but are not limited to, various interleukins (MacDonald et al. Inflamm. Bowel Dis. 2012 November; 18(11):2180-2189), TGF-β (Babyatsky et al. Gastroenterology 1996 April; 110(4):975-984; Gorelik et al. Nat. Rev. Immunol 2002 January; 2(1):46-53; Boirivant et al. Gastroenterology 2006 December; 131(6):1786-1798), annexin A1 (Babbin et al. J. Immunol 2008 October; 181 (7):5035-5044) and mimics (Kamaly et al. Proc. Natl. Acad.

Sci. U.S.A. 2013 April; 110(16):6506-6511), trefoil factors (Kjellev S. Cell. Mol. Life Sci. 2009 April; 66(8):1350-1369), bacterial immunomodulators (Jones et al. Cell Host Microbe 2008 April; 3(4):233-244; Foligne et al. Adv. Exp. Med. Biol. 2007; 603:361-366; Nedialkov et al. Infect. Immun. 1997 April; 65(4):1196-1203), helminthic immunomodulators (Elliott et al. Ann. N. Y. Acad. Sci. 2012 January; 1247:83-96; Hartmann et al. PLoS ONE 2013; 8(6):e68380; Girgis et al. PLoS Pathog. 2013 April; 9(4):e1003250), antibodies against inflammatory effectors (Scharl et al. Curr Drug Targets 2013 April) (e.g., such as infliximab (Knight et al. Mol. Immunol. 1993 November; 30(16):1443-1453; Present et al. N. Engl. J. Med. 1999 May; 340(18):1398-1405)) and the like.

The therapeutic effectiveness of engineered microbes generated in Examples II and III are assayed in mouse models of colitis.

Transiently Delivered EcN is Effective in Treating Colitis

EcN is reportedly as effective as mesalazine for maintaining remission of ulcerative colitis (Kruis et al. Gut 2004 November; 53(11):1617-1623; Rembacken et al. Lancet 1999 August; 354(9179):635-639). It exhibits anti-inflammatory properties (Behnsen et al. Cold Spring Harb Perspect Med 2013 March; 3(3):a010074) mediated through TLR-2/4-dependent signaling (Grabig et al. Infect. Immun. 2006 July; 74(7):4075-4082) and antagonizes adherent/invasive E. coli (Martinez-Medina et al. Inflamm. Bowel Dis. 2009 June; 15(6):872-882) linked to IBD (Barnich et al. Curr. Opin. Gastroenterol. 2007 January; 23(1):16-20). EcN has proven effective in mouse models of colitis (Grabig et al. Infect. Immun. 2006 July; 74(7):4075-4082; Schultz et al. Clin. Diagn. Lab. Immunol. 2004 March; 11(2):372-378; Kokesova et al. Folia Microbiol. (Praha) 2006; 51(5):478-484; Ukena et al. PLoS ONE 2007; 2(12):e1308; Garrido-Mesa et al. Biochem. Pharmacol. 2011 December; 82(12): 1891-1900; Schumann et al. Appl. Environ. Microbiol. 2012 March; 78(5):1513-1522; Jacobi et al. Gut Pathog 2012; 4(1):8; Gardlik et al. Folia Biol. (Praha) 2012; 58(6):238-245), but especially so when it is the sole strain colonizing germ-free mice (Hudcovic et al. Folia Microbiol. (Praha) 2007; 52(6):618-626), suggesting that it may be possible to maintain remission indefinitely by rendering EcN the dominant E. coli strain in the gut using the phage-immune strains and phages described herein.

Comparing Transient Versus Stably Colonized EcN in Mice

Stably-versus transiently-delivered EcN are studied in four groups of 8-week old female BALB/c mice treated with dextran sodium sulfate (DSS), a standard mouse model of colitis (Whittem et al. J Vis Exp 2010; (35)). Healthy controls will receive clean water while experimental groups will receive water with 5% DSS from day 5 to day 13. One group is stably colonized with phage-immune EcN on day 1 using the methods of Example II and given the same strain or saline by gavage to the other groups on days 2-13. Mice are weighed daily until they are sacrificed and histologically scored to evaluate inflammation (Whittem et al. J Vis Exp 2010; (35)).

Verifying Secretion of Active Effectors by E. coli

Four effectors have improved symptoms in mouse models of colitis, including DSS-treated mice, when delivered by engineered *Lactococcus lactis*: IL-10 (Steidler et al. Science 2000 August; 289(5483):1352-1355), TFF3 (Vandenbroucke et al. Gastroenterology 2004 August; 127(2):502-513), LcrV (Foligne et al. Gastroenterology 2007 September; 133(3):862-874), and anti-TNF nanobodies (Vandenbroucke et al. Mucosal Immunol 2010 January; 3(1):49-56). Active mammalian cytokines can be secreted by appropriately engineered E. coli (Zhang et al. Nat. Biotechnol. 2006 January; 24(1):100-104; Kotzsch et al. Protein Sci. 2011 March; 20(3):597-609; Pohlmann et al. J. Mol. Microbiol. Biotechnol. 2012; 22(1):1-9), but achieving high-level secretion may be difficult.

Culture supernatants are assayed using ELISA, microtiter plates, Western blotting, and macrophage culture as appropriate to determine which effector to carry forward (Vandenbroucke et al. Gastroenterology 2004 August; 127(2): 502-513; Vandenbroucke et al. Mucosal Immunol 2010 January; 3(1):49-56; Steidler et al. Science 2000 August; 289(5483):1352-1355; Foligne et al. Gastroenterology 2007 September; 133(3):862-874).

Using Mobile Elements to Engineer Native Cells to Secrete Effector

Mobile elements carrying an effector cassette or no cassette are used to modify resident E. coli strains within BALB/c mice according to the methods of Example III. A third group receives daily doses of MG1655 E. coli engineered with the expression cassette. All three groups receive water with 5% DSS from day 5 to day 13, while control mice receive water with no DSS. Mice are weighed daily until they are sacrificed and histologically scored for inflammation (Whittem et al. J Vis Exp 2010; (35)). Effector levels in each tissue section are quantitated and the fraction of effector-producing E. coli is measured by ELISA.

E. coli Population Levels in Mice

Because E. coli populations are much lower in mice than in humans (Tenaillon et al. Nat. Rev. Microbiol. 2010 March; 8(3):207-217), therapeutic efficacy in mice may be correspondingly lower. While promising for eventual use in patients, it may lead to false negative results in the methods described herein. To account for this, equivalent experiments are carried out using streptomycin-treated mice. While streptomycin treatment can cause inflammatory complications by altering the microbiota, the higher levels of E. coli in these mice may be necessary to observe positive effects.

The experiment is considered a moderate success if stably colonized bacteria are therapeutically effective as measured by histological scores and weight gain, is considered a success if stably colonized EcN or effector-secreting native strains are superior to transiently delivered E. coli, and is considered a complete success if these results are observed in conventional mice.

In summary, methods of determining whether stable populations of engineered enteric microbes can secrete enough effector molecules to treat inflammation in mice over an extended time period are described.

Example VI

Summary

Methods of combining the RNA-guided Cas9 nuclease with phages and horizontal gene transfer to precisely alter the cellular and genetic composition of microbial ecosystems are described herein. These methods are effective in simple laboratory cultures. These methods can be used to treat Shiga toxin-producing *E. coli* infections and can be used in mouse models of colitis. Success will lay the foundation for a new therapeutic paradigm based on precisely altering the cellular and genetic composition of the microbiota for the in situ treatment of disease. Of the many possible avenues to explore, the more promising include, but are not limited to: developing similar methods of modifying species such as *Clostridia* (Atarashi et al. Nature 2013 August; 500(7461):232-236) and *Bacteroides*, immunizing bacterial populations against antibiotic resistance genes such as NDM-1 (Cornaglia et al. Lancet Infect Dis 2011 May; 11(5):381-393), immunizing gut *E. coli* against virulence genes required for urinary tract infections (Lloyd et al. J. Bacteriol. 2007 May; 189(9):3532-3546), and in situ testing of effector combinations as potential therapeutics for IBD, obesity, and diabetes.

What is claimed is:

1. A method of altering a resident gut bacterial cell population in an individual's gut, comprising the steps of:
    depleting one or more target resident gut bacterial cells from the individual's gut by adding a dose of a bacteriophage to the individual's gut;
    releasing into the individual's gut a dose of an engineered bacterial cells having immunity against the bacteriophage; and
    allowing the engineered bacterial cells to colonize the individual's gut in place of the depleted target resident gut bacterial cells,
    wherein the engineered bacterial cell expresses a Cas enzyme and comprises a first foreign nucleic acid sequence encoding a plurality of RNA sequences having spacer sequences complementary to conserved nucleic acid sequences of the bacteriophage, wherein the engineered bacterial cell expresses the foreign nucleic acid sequence encoding the plurality of RNA sequences, and wherein the Cas enzyme interacts with one or more of the plurality of RNA sequences and cleaves a conserved nucleic acid sequence of the bacteriophage.

2. The method of claim 1, wherein the engineered bacterial cell has Cas9-mediated resistance.

3. The method of claim 1, wherein the Cas enzyme is Cas9.

4. The method of claim 1, wherein the engineered bacterial cell has further comprises a second foreign nucleic acid encoding the Cas enzyme.

5. The method of claim 1, wherein the Cas enzyme is an orthogonal Cas9.

6. The method of claim 1, wherein at least five of the plurality of RNA sequences bind to consensus nucleic acid sequences of the bacteriophage.

7. The method of claim 1, wherein at least five of the plurality of RNA sequences bind to complementary exogenous virulence nucleic acid sequences.

8. The method of claim 1, wherein one or more of the plurality of RNA sequences is complementary to an exogenous nucleic acid sequence encoding a product that is toxic to the target resident gut bacterial cells or to a host of the target resident gut bacterial cells.

9. The method of claim 1, wherein the foreign nucleic acid sequence is provided as a mobile genetic element.

10. The method of claim 1, wherein the foreign nucleic acid sequence is introduced into the engineered bacterial cell by a method selected from the group consisting of bacterial conjugation, infection, transfection and transformation.

11. The method of claim 1, wherein the engineered bacterial cell is non-pathogenic to a host.

12. The method of claim 10, further comprising the step of integrating the foreign nucleic acid sequence into the genome of the engineered bacterial cell using homologous recombination.

13. The method of claim 12, wherein two or more foreign nucleic acid sequences are integrated into the genome of the engineered bacterial cell using homologous recombination.

14. The method of claim 1, wherein the plurality of RNA sequences is selected from the group consisting of pre-crRNA, crRNA, guide RNA, and any combinations thereof.

15. The method of claim 1, wherein the bacteriophage is a T4 or T7 bacteriophage.

* * * * *